US012780766B2

(12) United States Patent
Gu et al.

(10) Patent No.: US 12,780,766 B2
(45) Date of Patent: Nov. 3, 2026

(54) BIS(VINYLBENZYL) FLUORENE AND PREPARATION METHOD AND USE THEREOF, AND BIS(VINYLBENZYL) FLUORENE HYDROCARBON RESIN AND PREPARATION METHOD AND USE THEREOF

(71) Applicant: Shandong Xingshun New Material INC., Heze (CN)

(72) Inventors: Xiaoxing Gu, Heze (CN); Guoyuan Lu, Heze (CN)

(73) Assignee: Shandong Xingshun New Material INC., Heze (CN)

(*) Notice: Subject to any disclaimer, the term of this patent is extended or adjusted under 35 U.S.C. 154(b) by 83 days.

(21) Appl. No.: 18/874,413

(22) PCT Filed: Aug. 26, 2024

(86) PCT No.: PCT/CN2024/114514
§ 371 (c)(1),
(2) Date: Dec. 12, 2024

(87) PCT Pub. No.: WO2026/031280
PCT Pub. Date: Feb. 12, 2026

(65) Prior Publication Data
US 2026/0109658 A1 Apr. 23, 2026

(30) Foreign Application Priority Data
Aug. 9, 2024 (CN) ........................ 202411095175.5

(51) Int. Cl.
*C07C 13/547* (2006.01)
*C07C 13/567* (2006.01)

(52) U.S. Cl.
CPC ........ *C07C 13/547* (2013.01); *C07C 2603/18* (2017.05)

(58) Field of Classification Search
CPC ............................ C07C 13/547; C07C 13/567
See application file for complete search history.

(56) References Cited

U.S. PATENT DOCUMENTS 7,514,379 B2 4/2009 Nishiguchi et al.

FOREIGN PATENT DOCUMENTS

| | | | |
|---|---|---|---|
| CN | 1501899 | A | 6/2004 |
| JP | 2003-283076 | A | 10/2003 |
| WO | 2022/207741 | A1 | 10/2022 |

*Primary Examiner* — Catherine S Branch
(74) *Attorney, Agent, or Firm* — WCF IP

(57) ABSTRACT

Disclosed are a bis(vinylbenzyl) fluorene and a preparation method and use thereof, and a bis(vinylbenzyl) fluorene hydrocarbon resin and a preparation method and use thereof, belonging to the technical field of high-frequency substrate materials. The bis(vinylbenzyl) fluorene is selected from 9,9-bis(2-vinylbenzyl)-9H-fluorene having a structure shown in formula I and 9,9-bis(4-vinylbenzyl)-9H-fluorene having a structure shown in formula II:

formula I

, (Continued)

-continued
formula II
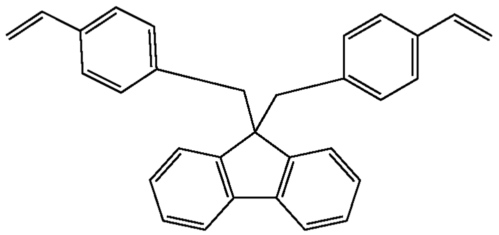
,
the 9,9-bis(2-vinylbenzyl)-9H-fluorene has a monoclinic crystal system; and the 9,9-bis(4-vinylbenzyl)-9H-fluorene has a triclinic crystal system.
14 Claims, 16 Drawing Sheets

Crystal structure ('O' represents H atom)

Unit-cell stacking diagram

Crystal structure ('O' represents H atom)

Unit-cell stacking diagram

BIS(VINYLBENZYL) FLUORENE AND PREPARATION METHOD AND USE THEREOF, AND BIS(VINYLBENZYL) FLUORENE HYDROCARBON RESIN AND PREPARATION METHOD AND USE THEREOF

CROSS REFERENCE TO RELATED APPLICATION

The present application is a national stage application of International Patent Application No. PCT/CN2024/114514, filed on Aug. 26, 2024, which claims priority to the Chinese patent application No. CN202411095175.5, filed with China National Intellectual Property Administration on Aug. 9, 2024, and entitled "BIS(VINYLBENZYL) FLUORENE AND PREPARATION METHOD AND USE THEREOF, AND BIS(VINYLBENZYL) FLUORENE HYDROCARBON RESIN AND PREPARATION METHOD AND USE THEREOF". The disclosure of the two applications is incorporated by references herein in their entireties as part of the present application.

TECHNICAL FIELD

The present disclosure relates to the technical field of high-frequency substrate materials, and in particular to a bis(vinylbenzyl) fluorene and a preparation method and use thereof, and a bis(vinylbenzyl) fluorene hydrocarbon resin and a preparation method and use thereof.

BACKGROUND

A resin with a low dielectric constant ($D_k$) and a low dielectric dissipation factor ($D_f$) is a key material for a high-frequency substrate, an antenna and the like in microelectronic field. A modified polyphenylene oxide (MPPO) terminated with vinylbenzyl or acryloyl has a lower dielectric constant and a lower dielectric dissipation factor, thus being widely used as a laminated board material for a printed circuit board (PCB). However, with the rapid development of 5G/6G communication, AR/VR and artificial intelligence, electronic products tend to require a higher transmission rate, a higher frequency and a larger capacity to transmit sounds, videos and data. Meanwhile, electronic products tend to be increasingly light, thin and small. In order to maintain a high transmission rate and signal integrity, a printed circuit board, as a core component of an electronic product, is required to have a resin material with a lower dielectric constant and a lower dielectric dissipation factor. Therefore, the further reduction of the dielectric constant and dielectric loss of resin materials is a key technical problem that is urgently required to be solved at present.

With a unique Cardo structure, a 9,9-disubstituted fluorenyl hydrocarbon derivative has good photoelectric properties such as a lower dielectric constant, a higher refractive index and a higher transparency, and has a good heat resistance, a good moisture resistance and a good solubility in an organic solvent, thus being widely used as a microelectronic device material.

JP2003283076A discloses a mixture prepared by reacting vinylbenzyl chloride and allyl chloride with fluorene, and the thermosetting resin of the mixture has a dielectric constant (5 GHz) of 4.0 and a dielectric dissipation factor (5 GHz) of 0.0035, where the vinylbenzyl chloride is a mixture of a meta isomer and a para isomer in a mass ratio of 1:1. CN1501899A and U.S. Pat. No. 7,514,379B2 disclose a mixture of a meta isomer of 9,9-bis(vinylbenzyl)-9H-fluorene and a para isomer of 9,9-bis(vinylbenzyl)-9H-fluorene, with a melting point of 142° C., prepared by reacting vinylbenzyl chloride with fluorene, and the thermosetting resin of the mixture has a dielectric constant (1 MHz) of 2.65 and a dielectric dissipation factor (1 MHz) of 0.0013, where the vinylbenzyl chloride is a mixture of a meta isomer and a para isomer in a mass ratio of 1:1. WO2022207741A1 discloses a composition material including a mixture of a vinylbenzyl indene and a 9,9-bis(vinylbenzyl)-9H-fluorene containing a meta isomer, and bismaleimide; and the thermosetting laminated material of the composition material has a dielectric constant (10 GHz) of 2.55 and a dielectric dissipation factor (10 GHz) of 0.00089. However, none of the aforementioned 9,9-disubstituted fluorenyl hydrocarbon derivatives has been obtained a single isomer, and all of the 9,9-disubstituted fluorenyl hydrocarbon derivatives are a mixture containing a meta isomer (9,9-bis(3-vinylbenzyl)-9H-fluorene). The meta isomer of 9,9-disubstituted fluorenyl hydrocarbon derivative has a large molecular polarity, a higher melting point, a poor solubility in an organic solvent, and a poor compatibility with an alkenyl resin, resulting in that the dielectric dissipation factor of thermosetting resin is not low enough.

SUMMARY

In view of this, an object of the present disclosure is to provide a bis(vinylbenzyl) fluorene and a preparation method and use thereof, and a bis(vinylbenzyl) fluorene hydrocarbon resin free of a meta isomer and a preparation method and use thereof. The bis(vinylbenzyl) fluorene provided by the present disclosure has a high purity and is free of a meta isomer, and the bis(vinylbenzyl) fluorene hydrocarbon resin prepared using the bis(vinylbenzyl) fluorene as a raw material has a small dielectric dissipation factor and a low dielectric constant.

In order to achieve the aforementioned object, the present disclosure provides the following technical solutions.

The present disclosure provides a bis(vinylbenzyl) fluorene, which is selected from the group consisting of 9,9-bis(2-vinylbenzyl)-9H-fluorene (abbreviated to o,o-BVBF) having a structure shown in formula I and 9,9-bis(4-vinylbenzyl)-9H-fluorene (abbreviated to p,p-BVBF) having a structure shown in formula II:

formula I

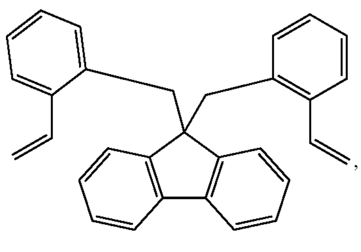
, formula II

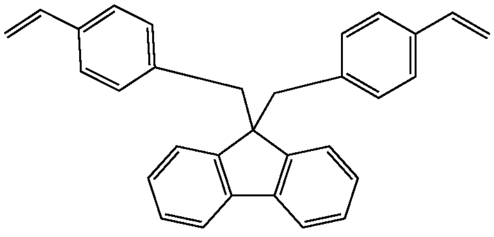
;

wherein the 9,9-bis(2-vinylbenzyl)-9H-fluorene has a monoclinic crystal system; and the 9,9-bis(4-vinylbenzyl)-9H-fluorene has a triclinic crystal system.

The present disclosure also provides a method for preparing the bis(vinylbenzyl) fluorene described in the aforementioned technical solutions, including:

mixing fluorene, vinylbenzyl chloride, a basic reagent, a polymerization inhibitor, a phase-transfer catalyst, and an organic solvent, and subjecting a resulting mixture to phase transfer reaction, to obtain the bis(vinylbenzyl) fluorene; where the vinylbenzyl chloride is selected from the group consisting of 2-vinylbenzyl chloride and 4-vinylbenzyl chloride.

In some embodiments, the phase-transfer catalyst includes at least one selected from the group consisting of a quaternary ammonium salt, a quaternary phosphonium salt, and polyethylene glycol; a mass of the phase-transfer catalyst is 10-35% of a mass of the fluorene; the organic solvent includes at least one selected from the group consisting of an aromatic hydrocarbon, an aliphatic hydrocarbon, petroleum ether, and acetonitrile.

In some embodiments, the phase transfer reaction is performed at a temperature of 25-45° C. for 12-18 h, and the phase transfer reaction is performed with stirring.

In some embodiments, the polymerization inhibitor includes at least one selected from the group consisting of nitromethane, nitrobenzene, o-nitrophenol, phenothiazine, 2-phenylnaphthylamine, hydroquinone, catechol, p-methoxyphenol, 2,6-di-tert-butyl-p-cresol, p-tert-butylcatechol, 2,2,6,6-tetramethylpiperidine oxynitride, and 2,2,6,6-tetramethyl-4-hydroxypiperidine oxynitride; and a mass of the polymerization inhibitor is 0.01-0.5% of a mass of vinylbenzyl chloride.

In some embodiments, a molar ratio of the fluorene to the vinylbenzyl chloride is in a range of 1:2 to 1:2.5.

The present disclosure also provides a bis(vinylbenzyl) fluorene hydrocarbon resin, which is prepared from a raw material including a bis(vinylbenzyl) fluorene, where the bis(vinylbenzyl) fluorene is at least one selected from the group consisting of 9,9-bis(2-vinylbenzyl)-9H-fluorene having a structure shown in formula I and 9,9-bis(4-vinylbenzyl)-9H-fluorene having a structure shown in formula II:

formula I

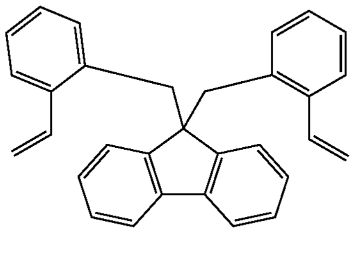

, formula II

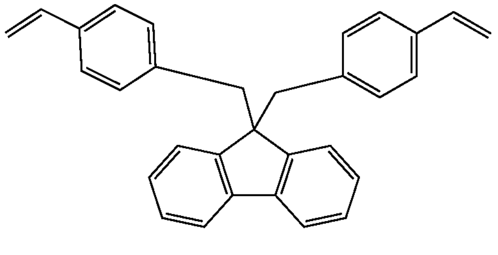

.

In some embodiments, under the condition that the bis (vinylbenzyl) fluorene is a mixture of the 9,9-bis(2-vinylbenzyl)-9H-fluorene and the 9,9-bis(4-vinylbenzyl)-9H-fluorene, a content of the 9,9-bis(2-vinylbenzyl)-9H-fluorene in the mixture is not less than 5 wt %.

The present disclosure also provides a method for preparing the bis(vinylbenzyl) fluorene hydrocarbon resin described in the aforementioned technical solutions, including: subjecting the bis(vinylbenzyl) fluorene to thermal solidification to obtain the bis(vinylbenzyl) fluorene hydrocarbon resin.

The present disclosure also provides use of the bis(vinylbenzyl) fluorene hydrocarbon resin described in the aforementioned technical solutions or the bis(vinylbenzyl) fluorene hydrocarbon resin prepared by the method described in the aforementioned technical solutions in a high-frequency substrate.

9,9-bis(vinylbenzyl)-9H-fluorene has a variety of constitutional isomers, and the stereo-configuration and crystal forms of the bis(vinylbenzyl) fluorene isomers with different structures may affect physical properties such as dielectric constant, dielectric dissipation factor and the solubility in an organic solvent. The bis(vinylbenzyl) fluorene provided by the present disclosure has a high purity (higher than 99%), and is free of meta isomers (9,9-bis(3-vinylbenzyl)-9H-fluorene shown in formula III and 9-(3-vinylbenzyl)-9-(4-vinylbenzyl)-9H-fluorene shown in formula IV).

formula III

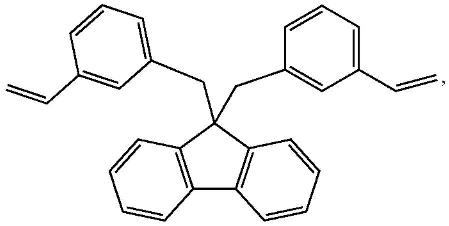

, formula IV

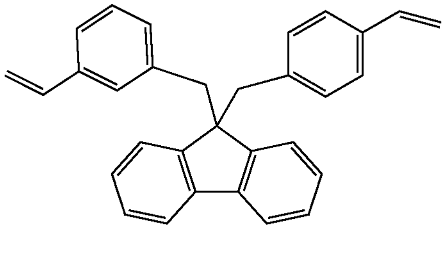

.

The 9,9-bis(2-vinylbenzyl)-9H-fluorene and 9,9-bis(4-vinylbenzyl)-9H-fluorene provided by the present disclosure are soluble in toluene and/or 2-butanone at room temperature (25° C.) to form a clear solution, thus being suitable for use as a crosslinking agent for an alkenyl resin component in a high-frequency substrate. All of the bis(vinylbenzyl) fluorene hydrocarbon resins provided by the present disclosure and prepared using 9,9-bis(2-vinylbenzyl)-9H-fluorene and 9,9-bis(4-vinylbenzyl)-9H-fluorene as raw materials have a low dielectric constant and a low dielectric dissipation factor.

As shown in the test results of examples, a bis(vinylbenzyl) fluorene hydrocarbon resin using 9,9-bis(2-vinylbenzyl)-9H-fluorene as a raw material has a dielectric constant $D_k$ (10 GHz) of 2.8 and a dielectric dissipation factor $D_f$ (10 GHz) of 0.00032; a bis(vinylbenzyl) fluorene hydrocarbon resin using 9,9-bis(4-vinylbenzyl)-9H-fluorene as a raw material has a dielectric constant $D_k$ (10 GHz) of 2.8 and a dielectric dissipation factor $D_f$ (10 GHz) of 0.00047; and thus the bis(vinylbenzyl) fluorene hydrocarbon resins have a low dielectric constant and a low dielectric dissipation factor.

The bis(vinylbenzyl) fluorene hydrocarbon resin provided by the present disclosure and prepared using a mixture of 9,9-bis(2-vinylbenzyl)-9H-fluorene and 9,9-bis(4-vinylbenzyl)-9H-fluorene in any ratio also has a low dielectric constant and a low dielectric dissipation factor, and a higher content of 9,9-bis(2-vinylbenzyl)-9H-fluorene results in a smaller dielectric dissipation factor of the bis(vinylbenzyl) fluorene hydrocarbon resin. Under the condition that the content of 9,9-bis(2-vinylbenzyl)-9H-fluorene is 20 wt % or higher, the dielectric dissipation factor of the bis(vinylbenzyl) fluorene hydrocarbon resin is 0.00044 or less.

Compared with a 1,2-bis(4-vinylphenyl) ethane resin, a mixture of a meta isomer and a para isomer of 9,9-bis (vinylbenzyl)-9H-fluorene, and a mixture of an ortho isomer, a meta isomer and a para isomer of 9,9-bis(vinylbenzyl)-9H-fluorene, the bis(vinylbenzyl) fluorene hydrocarbon resin provided by the present disclosure and prepared using one or both of 9,9-bis(2-vinylbenzyl)-9H-fluorene and 9,9-bis(4-vinylbenzyl)-9H-fluorene as a raw material has a significantly-reduced dielectric dissipation factor. Additionally, compared with 1,2-bis(4-vinylphenyl) ethane or a 9,9-bis (vinylbenzyl)-9H-fluorene containing a meta isomer, the 9,9-bis(2-vinylbenzyl)-9H-fluorene and 9,9-bis(4-vinylbenzyl)-9H-fluorene provided by the present disclosure has significantly-improved solubility in toluene or 2-butanone. Thus, the bis(vinylbenzyl) fluorene hydrocarbon resin provided by the present disclosure has good application prospects in use as a principal resin in a high-frequency substrate.

The method for preparing bis(vinylbenzyl) fluorene provided by the present disclosure results in a single constitutional isomer (9,9-bis(2-vinylbenzyl)-9H-fluorene, 9,9-bis (4-vinylbenzyl)-9H-fluorene), namely, a high-purity compound, and has advantages of a simple process, simple operations, and a low cost, thus being suitable for industrialized production.

DETAILED DESCRIPTION OF THE EMBODIMENTS

Figure 1:
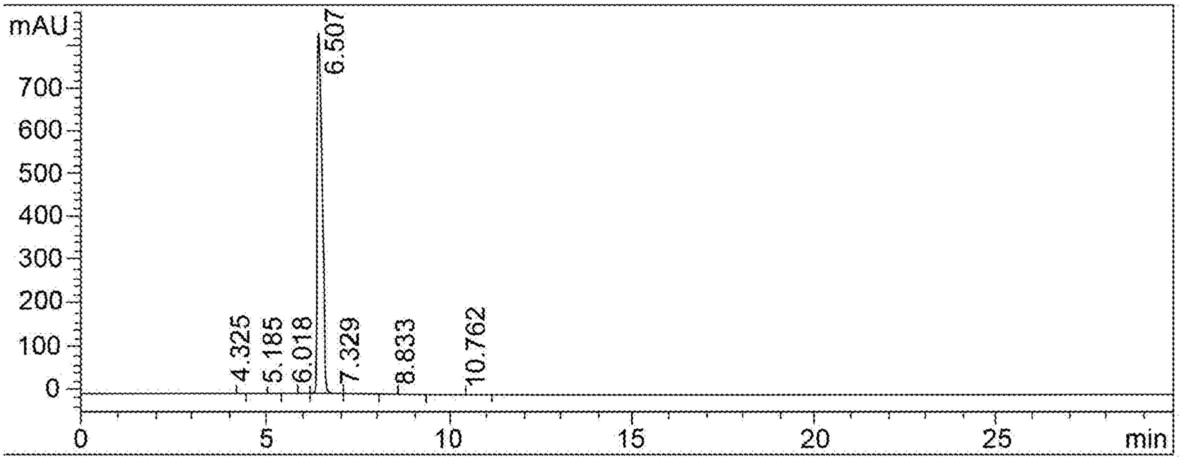
FIG. 1 shows a high performance liquid chromatography (HPLC) spectrum of 9,9-bis(2-vinylbenzyl)-9H-fluorene prepared in Example 1.

The present disclosure provides a bis(vinylbenzyl) fluorene which is 9,9-bis(2-vinylbenzyl)-9H-fluorene having a structure shown in formula I or 9,9-bis(4-vinylbenzyl)-9H-fluorene having a structure shown in formula II:

formula I

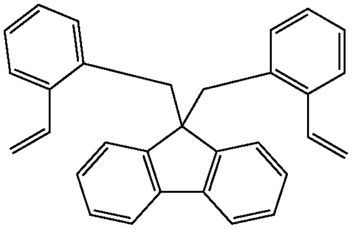

, formula II

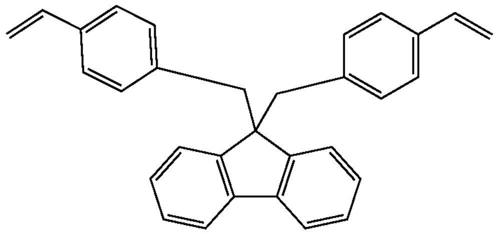

.

In the present disclosure, the 9,9-bis(2-vinylbenzyl)-9H-fluorene (crystal) has a monoclinic crystal system. In some embodiments, the 2θ characteristic peaks of the powder X-ray diffraction analysis of the 9,9-bis(2-vinylbenzyl)-9H-fluorene includes: 11.9°, 12.3°, 14.2°, 15.4°, 18.5°, 19.2°, 20.0°, 20.7°, 22.2°, 23.7° and 24.7°. In some embodiments, the 9,9-bis(2-vinylbenzyl)-9H-fluorene has a melting point of 124-126° C., and preferably 124.0-125.5° C. In some embodiments, the 9,9-bis(2-vinylbenzyl)-9H-fluorene has a purity of larger than 99.0%. In some embodiments, the 9,9-bis(2-vinylbenzyl)-9H-fluorene has a space group of $P2_1/c$. In some embodiments, the 9,9-bis(2-vinylbenzyl)-9H-fluorene has unit-cell dimensions as follows: a=20.0139 (5)Å, α=90°, b=10.9697(3)Å, β=96.243(2°), c=10.1983(3) Å, and γ=90°.

In the present disclosure, the 9,9-bis(4-vinylbenzyl)-9H-fluorene (crystal) has a triclinic crystal system. In some embodiments, the 2θ characteristic peaks of the powder X-ray diffraction analysis of the 9,9-bis(4-vinylbenzyl)-9H-fluorene includes: 11.1°, 12.0°, 18.6°, 19.1°, 20.0°, 22.1°, 23.6°, 24.0° and 24.6°. In some embodiments, the 9,9-bis (4-vinylbenzyl)-9H-fluorene has a melting point of 118-120° C., and preferably 118.4-119.8° C. In some embodiments, the 9,9-bis(4-vinylbenzyl)-9H-fluorene has a purity of larger than 99.0%. In some embodiments, the 9,9-bis(4-vinylbenzyl)-9H-fluorene has a space group of $P\bar{1}$, and unit-cell dimensions as follows: a=10.6519(6)λ, α=94.299(2°), b=14.6326(7)Å, β=92.157(2°), c=14.7009(8)Å, and γ=91.265(3°).

The bis(vinylbenzyl) fluorene hydrocarbon resin provided by the present disclosure and prepared using one of 9,9-bis (2-vinylbenzyl)-9H-fluorene and 9,9-bis(4-vinylbenzyl)-9H-fluorene or a mixture thereof in any ratio as a raw material has a very low dielectric constant and a very low dielectric dissipation factor, and a higher content of 9,9-bis (2-vinylbenzyl)-9H-fluorene results in a smaller dielectric dissipation factor of bis(vinylbenzyl) fluorene hydrocarbon resin. Additionally, the 9,9-bis(2-vinylbenzyl)-9H-fluorene and 9,9-bis(4-vinylbenzyl)-9H-fluorene provided by the present disclosure have higher solubility in toluene and 2-butanone. The use of one of 9,9-bis(2-vinylbenzyl)-9H-fluorene and 9,9-bis(4-vinylbenzyl)-9H-fluorene or a mixture thereof in any ratio as a crosslinking agent for an alkenyl resin component also have good application prospects. The bis(vinylbenzyl) fluorene hydrocarbon resin prepared from one of 9,9-bis(2-vinylbenzyl)-9H-fluorene and 9,9-bis(4-vinylbenzyl)-9H-fluorene or a mixture thereof has good application prospects in use as a principal resin in a high-frequency substrate.

The present disclosure provides a method for preparing the bis(vinylbenzyl) fluorene described in the aforementioned technical solutions, which includes the steps of: mixing fluorene, vinylbenzyl chloride, a basic reagent, a polymerization inhibitor, a phase-transfer catalyst, and an organic solvent, and subjecting a resulting mixture to phase transfer reaction to obtain the bis(vinylbenzyl) fluorene; where the vinylbenzyl chloride is 2-vinylbenzyl chloride or 4-vinylbenzyl chloride.

Unless otherwise specified, the materials and equipment used in the present disclosure are commercially available in the art.

In some embodiments of the present disclosure, a molar ratio of the fluorene to the vinylbenzyl chloride is in a range of 1: 2-2.5, preferably 1:2.1-2.4, and further preferably 1:2.2-2.3. In some embodiments of the present disclosure, both the 2-vinylbenzyl chloride (CAS: 22570-84-9) and 4-vinylbenzyl chloride (CAS: 1592-20-7) are produced by Shandong Xingshun New Materials Co., Ltd., China. In some embodiments, the 2-vinylbenzyl chloride has a purity of 99.0%. In some embodiments, the 4-vinylbenzyl chloride has a purity of 99.5%.

In some embodiments of the present disclosure, the basic reagent includes at least one of an alkali metal hydroxide and an alkali metal alkoxide. In some embodiments, the alkali metal hydroxide includes at least one of sodium hydroxide, potassium hydroxide, and lithium hydroxide, and preferably is potassium hydroxide. In some embodiments the alkali metal alkoxide includes at least one of sodium ethoxide, potassium ethoxide, sodium methoxide, potassium methoxide, sodium isopropoxide, potassium isopropoxide, sodium tert-butoxide and potassium tert-butoxide, and preferably is potassium tert-butoxide. In some embodiments of the present disclosure, a molar ratio of the fluorene to the basic reagent is in a range of 1:1.8-5, and preferably 1: 2-4, more preferably 1: 2-3.

In some embodiments of the present disclosure, the polymerization inhibitor includes at least one of nitromethane, nitrobenzene, o-nitrophenol, phenothiazine, 2-phenylnaphthylamine, hydroquinone, catechol, p-methoxyphenol, 2,6-di-tert-butyl-p-cresol, p-tert-butyl catechol, 2,2,6,6-tetramethylpiperidine oxynitride, and 2,2,6,6-tetramethyl-4-hydroxypiperidine oxynitride (polymerization inhibitor 701). In some embodiments of the present disclosure, a mass of the polymerization inhibitor is 0.01-0.5%, preferably 0.1-0.4%, more preferably 0.2-0.3% of a mass of vinylbenzyl chloride.

In some embodiments of the present disclosure, the phase-transfer catalyst includes at least one of a quaternary ammonium salt, a quaternary phosphonium salt, and polyethylene glycol (PEG), and preferably is polyethylene glycol. In some embodiments, the polyethylene glycol has a number-average molecular weight of 200-600, and preferably 400-600. In some embodiments, the polyethylene glycol includes at least one of PEG-200, PEG-400, and PEG-600. In some embodiments of the present disclosure, a mass of the transfer catalyst is 10-35%, preferably 20-30% of a mass of fluorene.

In some embodiments of the present disclosure, the organic solvent includes at least one of an aromatic hydrocarbon, an aliphatic hydrocarbon, petroleum ether, and acetonitrile, preferably is an aromatic hydrocarbon or acetonitrile. In some embodiments, the aromatic hydrocarbon includes at least one of toluene, xylene, and ethyl benzene, and preferably is toluene. In some embodiments, the aliphatic hydrocarbon includes at least one of cyclohexane, n-hexane, and n-heptane. In some embodiments of the present disclosure, a ratio of the mass of the fluorene to the volume of the organic solvent is in a range of 1 g: 3-8 mL, and preferably 1 g: 5 mL.

In some embodiments of the present disclosure, the phase transfer reaction is performed at a temperature of 25-45° C., preferably 30-40° C., and further preferably 30-35° C. In some embodiments, the phase transfer reaction is performed for 12-18 h, preferably 13-16 h, and further preferably 14-15 h. In some embodiments, the phase transfer reaction is performed with stirring. In some embodiments, the phase transfer reaction is performed at a stirring speed of 200-500 r/min, and preferably 300-400 r/min. In specific embodiments of the present disclosure, the phase transfer reaction is stopped when the content of fluorene in the reaction system is smaller than 1 wt %.

In some embodiments of the present disclosure, the method includes a post-treatment after the phase transfer reaction. In some embodiments, the post-treatment includes the steps of: subjecting a reaction system obtained by the phase transfer reaction to a first concentration, adding water and toluene thereto, and layering; subjecting a resulting organic phase to a washing with a saturated ammonium chloride solution, a washing with water until neutral, a second concentration, and recrystallization in sequence, and subjecting a resulting system to a solid-liquid separation; and drying a resulting solid component to obtain the bis (vinylbenzyl) fluorene.

In the present disclosure, there are no particular limitations on the first concentration and the second concentration, a concentration method known to those skilled in the art may be used as long as the solvent is removed, such as evaporation or reduced-pressure distillation.

In some embodiments of the present disclosure, the solvent used for the recrystallization includes at least one of an aromatic hydrocarbon solvent, a ketone solvent, an ether solvent, an alcohol solvent, and acetonitrile. In some embodiments, the aromatic hydrocarbon solvent includes at least one of toluene, xylene, ethyl benzene, and cumene. In some embodiments, the ketone solvent includes at least one of acetone, 2-butanone, and methyl isobutyl ketone. In some embodiments, the ether solvent includes at least one of methyl tert-butyl ether, tetrahydrofuran, methyl tetrahydrofuran, and anisole. In some embodiments, the alcohol solvent includes at least one of methanol, ethanol, and isopropanol. In some embodiments, the solvent used for the recrystallization is a mixed toluene-methanol solvent or a mixed toluene-acetonitrile solvent. In some embodiments, a volume ratio of the toluene to the methanol in the mixed toluene-methanol solvent is in a range of 1:0.1-0.6, and preferably 1:0.2-0.4. In some embodiments, a volume ratio of the toluene to the acetonitrile in the mixed toluene-acetonitrile solvent is in a range of 1:0.1-0.6, and preferably 1:0.2-0.4. In some embodiments of the present disclosure, the recrystallization includes the steps of: heating until being fully dissolved, cooling to a temperature of −10° C. to 20° C., and subjecting a resulting system to crystallization at a constant temperature. In some embodiments, the cooling is performed at a cooling rate of 0.2-1° C./min, and preferably 0.4-0.5° C./min. In some embodiments, the crystallization at constant temperature is performed at a temperature of 5-10° C.

In the present disclosure, there are no particular limitations on the solid-liquid separation. A solid-liquid separation method known to those skilled in the art may be adopted, such as filtration, suction filtration, or centrifugation.

In some embodiments of the present disclosure, the drying is performed at a temperature of 70-110° C., and preferably 80-90° C. In the present disclosure, there are no particular limitations on a time for the drying, so long as it is dried to reach a constant weight.

The present disclosure also provides use of the bis(vinylbenzyl) fluorene described in the aforementioned technical solutions or the bis(vinylbenzyl) fluorene prepared by the method described in the aforementioned technical solutions in a high-frequency substrate. In some embodiments of the present disclosure, the use refers to use as a crosslinking agent in a high-frequency substrate. In some embodiments, the crosslinking agent is used to crosslink an alkenyl resin component. In some embodiments, the alkenyl resin component includes a polyphenylene oxide end-modified with vinyl. In some embodiments of the present disclosure, the bis(vinylbenzyl) fluorene is used as a crosslinking agent in a high-frequency substrate. In some embodiments, the bis (vinylbenzyl) fluorene hydrocarbon resin is used as a principal resin for a high-frequency substrate. In some embodiments, the 9,9-bis(2-vinylbenzyl)-9H-fluorene, 9,9-bis(4-vinylbenzyl)-9H-fluorene, and a mixture thereof in any ratio provided by the present disclosure are each dissolved in toluene and 2-butanone in a compound-to-solvent mass ratio of 1:1 to form a clear solution, and each have high solubility in toluene and 2-butanone, thus having good prospects in the application as a crosslinking agent for an alkenyl resin component in a high-frequency substrate.

The present disclosure also provides a bis(vinylbenzyl) fluorene hydrocarbon resin prepared from a raw material including a bis(vinylbenzyl) fluorene, where the bis(vinylbenzyl) fluorene is at least one of 9,9-bis(2-vinylbenzyl)-9H-fluorene having a structure shown in formula I and 9,9-bis(4-vinylbenzyl)-9H-fluorene having a structure shown in formula II:

formula I

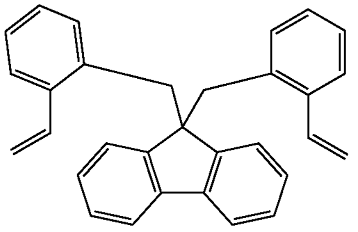

, formula II

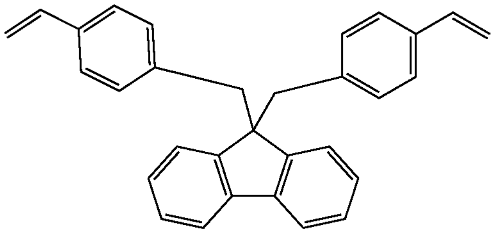

,

In the present disclosure, under the condition that the bis(vinylbenzyl) fluorene is a mixture of 9,9-bis(2-vinylbenzyl)-9H-fluorene and 9,9-bis(4-vinylbenzyl)-9H-fluorene, there are no particular limitations on the mass ratio of 9,9-bis(2-vinylbenzyl)-9H-fluorene to 9,9-bis(4-vinylbenzyl)-9H-fluorene in the mixture, and any ratio is possible. In particular, in some embodiments, the content of 9,9-bis(2-vinylbenzyl)-9H-fluorene in the mixture is 5 wt % or higher, preferably 10 wt % or higher, specifically 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt % or 95 wt %. In the present disclosure, a higher content of 9,9-bis(2-vinylbenzyl)-9H-fluorene in the mixture results in a smaller dielectric dissipation factor of the bis(vinylbenzyl) fluorene hydrocarbon resin. Under the condition that the content of 9,9-bis(2-vinylbenzyl)-9H-fluorene is higher than 20 wt %, the bis(vinylbenzyl) fluorene hydrocarbon resin has a $D_k$ (10 GHz) of 2.8 and a $D_f$ (10 GHz) less than 0.00044.

The present disclosure also provides a method for preparing the bis(vinylbenzyl) fluorene hydrocarbon resin described in the aforementioned technical solutions, including: subjecting a bis(vinylbenzyl) fluorene to thermal solidification to obtain the bis(vinylbenzyl) fluorene hydrocarbon resin.

In some embodiments of the present disclosure, the thermal solidification includes molten sample pouring. In some embodiments of the present disclosure, the thermal solidification is performed at a temperature of 200° C. and a pressure of 70-80 mmHg for 30 min.

The present disclosure also provides use of the bis(vinylbenzyl) fluorene described in the aforementioned technical solutions, the bis(vinylbenzyl) fluorene prepared by the method described in the aforementioned technical solutions, the bis(vinylbenzyl) fluorene hydrocarbon resin described in the aforementioned technical solutions, or the bis(vinylbenzyl) fluorene hydrocarbon resin prepared by the method described in the aforementioned technical solutions in a high-frequency substrate. In some embodiments of the present disclosure, the use refers to use as a principal resin or a crosslinking agent in a high-frequency substrate. In some embodiments, the crosslinking agent is used to crosslink an alkenyl resin component. In some embodiments, the alkenyl resin component includes a polyphenylene oxide end-modified with vinyl. In some embodiments of the present disclosure, the bis(vinylbenzyl) fluorene is used as a crosslinking agent in a high-frequency substrate. In some embodiments, the bis(vinylbenzyl) fluorene hydrocarbon resin is used as a principal resin in a high-frequency substrate.

The bis(vinylbenzyl) fluorene hydrocarbon resin provided by the present disclosure and prepared using one of 9,9-bis(2-vinylbenzyl)-9H-fluorene and 9,9-bis(4-vinylbenzyl)-9H-fluorene or a mixture thereof in any ratio as a raw material has a very low dielectric constant and a very low dielectric dissipation factor, and a higher content of 9,9-bis(2-vinylbenzyl)-9H-fluorene results in a smaller dielectric dissipation factor of the bis(vinylbenzyl) fluorene hydrocarbon resin. Additionally, in some embodiments, the 9,9-bis(2-vinylbenzyl)-9H-fluorene, 9,9-bis(4-vinylbenzyl)-9H-fluorene and a mixture thereof in any ratio provided by the present disclosure are each dissolved in toluene and 2-butanone in a compound-to-solvent mass ratio of 1:1 to form a clear solution, and thus each have high solubility in toluene and 2-butanone. The bis(vinylbenzyl) fluorene hydrocarbon resin has good prospects in the application as a principal resin in a high-frequency substrate.

For further illustration of the present disclosure, the bis(vinylbenzyl) fluorene and preparation method and use thereof, and the bis(vinylbenzyl) fluorene hydrocarbon resin and preparation method and use thereof provided by the present disclosure will be described in details below in conjunction with examples which could not be construed as limiting the scope of the present disclosure.

In the following examples, a 2-vinylbenzyl chloride (having an HPLC purity of 99.0% and produced by Shandong Xingshun New Materials Co., Ltd., China) and a 4-vinylbenzyl chloride (having an HPLC purity of 99.5% and produced by Shandong Xingshun New Materials Co., Ltd., China) were used.

Instruments and methods used for analyses and tests:

1. Purity determination method (HPLC): U.S. Agillent 1260 high-pressure liquid chromatograph; column type: Kromasil 100-5 C18 250 cm×4.6 mm; mobile phase being acetonitrile/methanol in a volume ratio of 9:1; flow rate being 0.8 mL/min; detection wavelength being 254 nm; sample injection volume being 2 μL; pump mode being binary high-pressure gradient.

2. Thermal analysis method: Pyris1 Thermal Analyzer (from Perkin Elemer) was used for DSC measurement, with a heating temperature range of 50-200° C. and a heat-up rate of 10° C./min.

3. Nuclear magnetic resonance spectrometry: Bruker AV 400 nuclear magnetic resonance spectrometer, with DMSO-$d_6$ as a solvent, and TMS as an internal standard.

4. Infrared spectrometry: NEXUS870 Fourier transform infrared spectrometer (FT-IR) (from NICOLET), tableting with potassium bromide.

5. Determination of single-crystal structure: Bruker D8 Venture single-crystal diffractometer, JY/T0588-2020 General Rules for Analysis Method of Molecular Structure.

6. Determination of dielectric constant $D_k$ (10 GHz) and dielectric dissipation factor $D_f$ (10 GHz): A molten sample pouring method (conditions of thermal solidification: a temperature being 200° C., a pressure being 70-80 mmHg, and a time being 30 min) was used to prepare 80 mm×80 mm×0.4 mm resin sheets, and measurement was performed by using U.S. Agilent N5230A vector network analyzer at a frequency of 10 GHz.

7. Powder x-ray diffraction spectrometry: Bruker D2 Phaser polycrystal diffractometer, JY/T0587-2020 General Rules for Analysis Method.

Example 1

Figure 6:
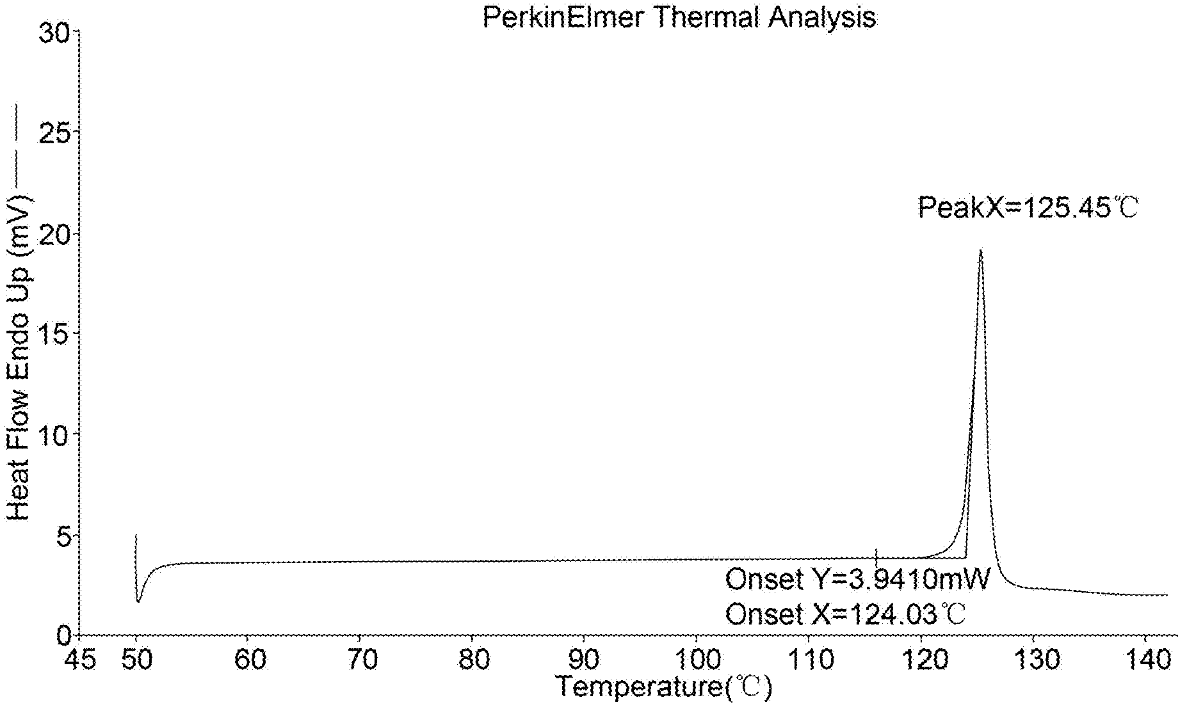
FIG. 6 shows a differential scanning calorimeter (DSC) spectrum of a thermoanalysis of 9,9-bis(2-vinylbenzyl)-9H-fluorene prepared in Example 1.

500 mL of acetonitrile, 1.4 mol of potassium hydroxide powder, 30 g of PEG-400, and 0.5 g of polymerization inhibitor 701 were added to a reaction flask, and 0.6 mol of fluorene and 1.4 mol of 2-vinylbenzyl chloride (HPLC, 99%) were then added thereto while stirring. At a temperature of 30-35° C. and a stirring speed of 350 r/min, the resulting mixture was subjected to reaction until the content of fluorene was lower than 1 wt % according to HPLC analysis. The reaction was stopped, and acetonitrile was distilled off. 500 mL of water and 500 mL of toluene were then added for layering. The organic phase was washed with a saturated ammonium chloride solution, and washed with water for 3 times (500 mL of water for each time) until neutral. Toluene was distilled off under reduced pressure, and a mixed solvent of toluene and methanol in a volume ratio of 1:0.3 was added thereto. The resulting mixture was heated until being fully dissolved, and cooled at a cooling rate of 0.5° C./min to 5° C. for crystallization at constant temperature. The resulting system was then filtered, and the resulting solid component was dried at 90° C. to constant weight so as to obtain 191.5 g of a 9,9-bis(2-vinylbenzyl)-9H-fluorene, i.e., o,o-BVBF, which was a white crystal having an HPLC purity (FIG. 1 and Table 1) of 99.4% and a melting point (thermal analysis DSC melting absorption peak, FIG. 6) of 124.0-125.5° C., with a yield of 80.1%.

TABLE 1

HPLC peak information of o,o-BVBF

| Peaks | Retention time/min | Type | Peak width/min | Peak area/mAU · s | Peak height/mAU | Peak area/% |
|---|---|---|---|---|---|---|
| 1 | 4.325 | VB | 0.1261 | 2.05417 | 0.258843 | 0.0310 |
| 2 | 5.185 | VB | 0.1087 | 3.17340 | 0.449067 | 0.0479 |
| 3 | 6.018 | BV | 0.1136 | 1.13122 | 0.153654 | 0.0171 |
| 4 | 6.507 | VV | 0.1195 | 6589.77441 | 850.62708 | 99.3721 |
| 5 | 7.329 | VB | 0.1429 | 26.97264 | 2.87846 | 0.4067 |
| 6 | 8.833 | VB | 0.1790 | 6.40461 | 0.506698 | 0.0966 |
| 7 | 10.762 | BB | 0.2181 | 1.90339 | 0.115719 | 0.0287 |

Figure 2:
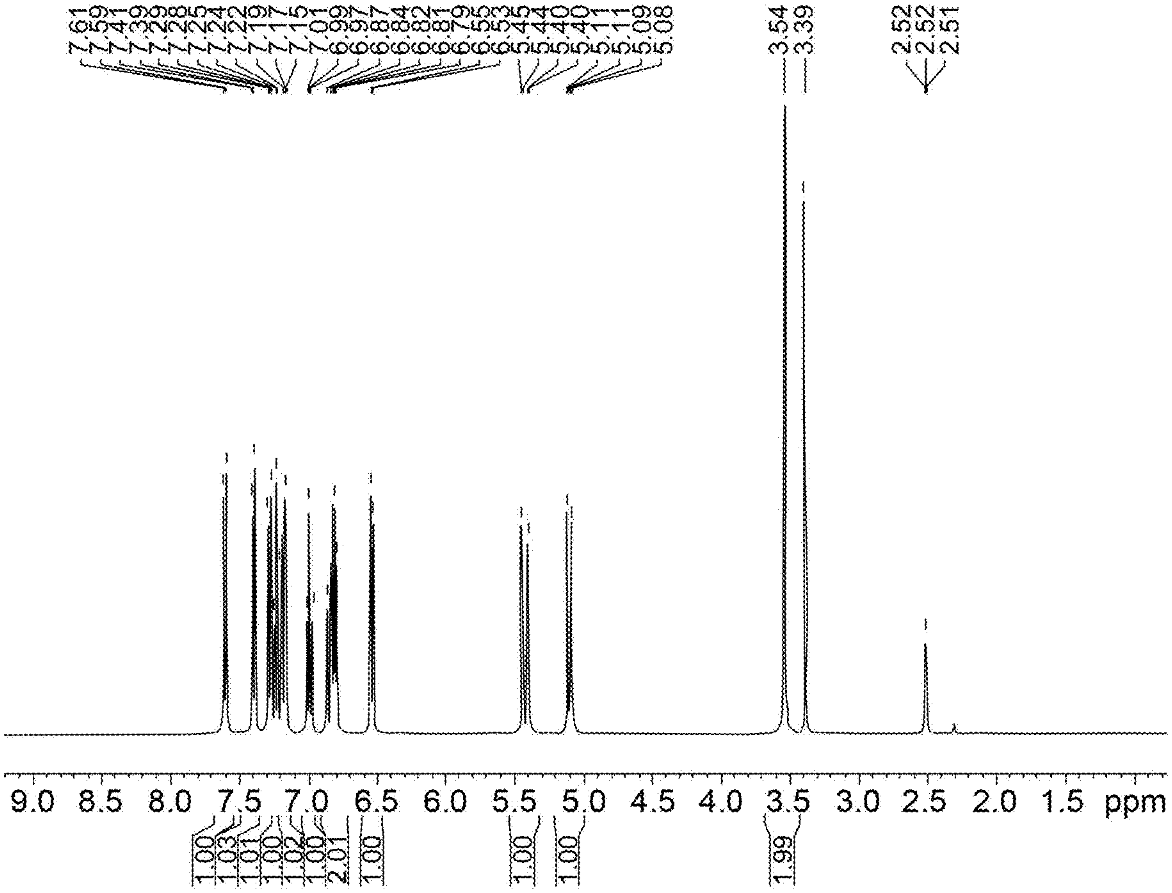
FIG. 2 shows an $^{1}H$ NMR spectrum of 9,9-bis(2-vinylbenzyl)-9H-fluorene prepared in Example 1.
Figure 3:
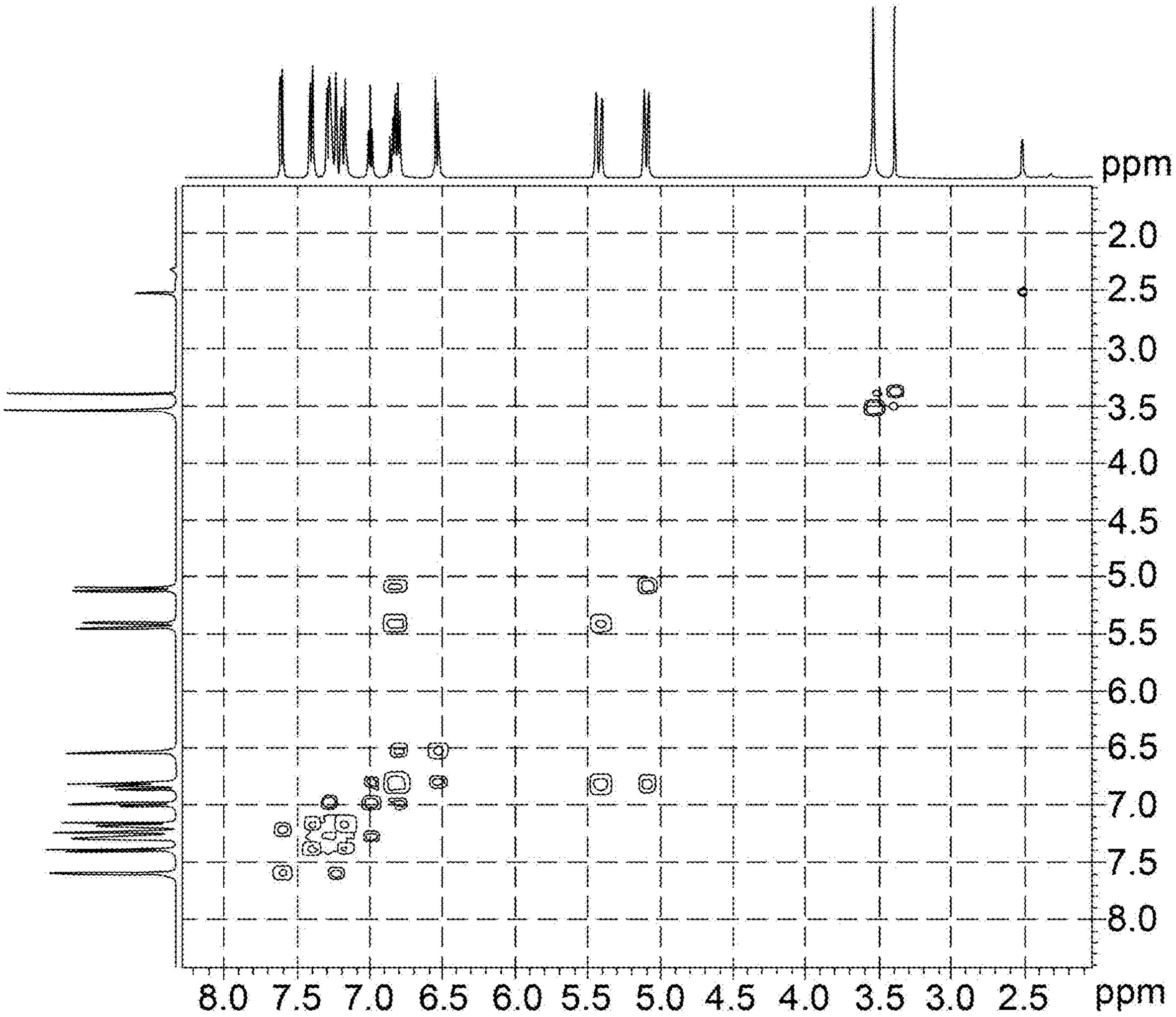
FIG. 3 shows a two-dimensional diagram of a DQF-COSY $^{1}H$-$^{1}H$ correlation nuclear magnetic resonance spectrum of 9,9-bis(2-vinylbenzyl)-9H-fluorene prepared in Example 1.
Figure 4:
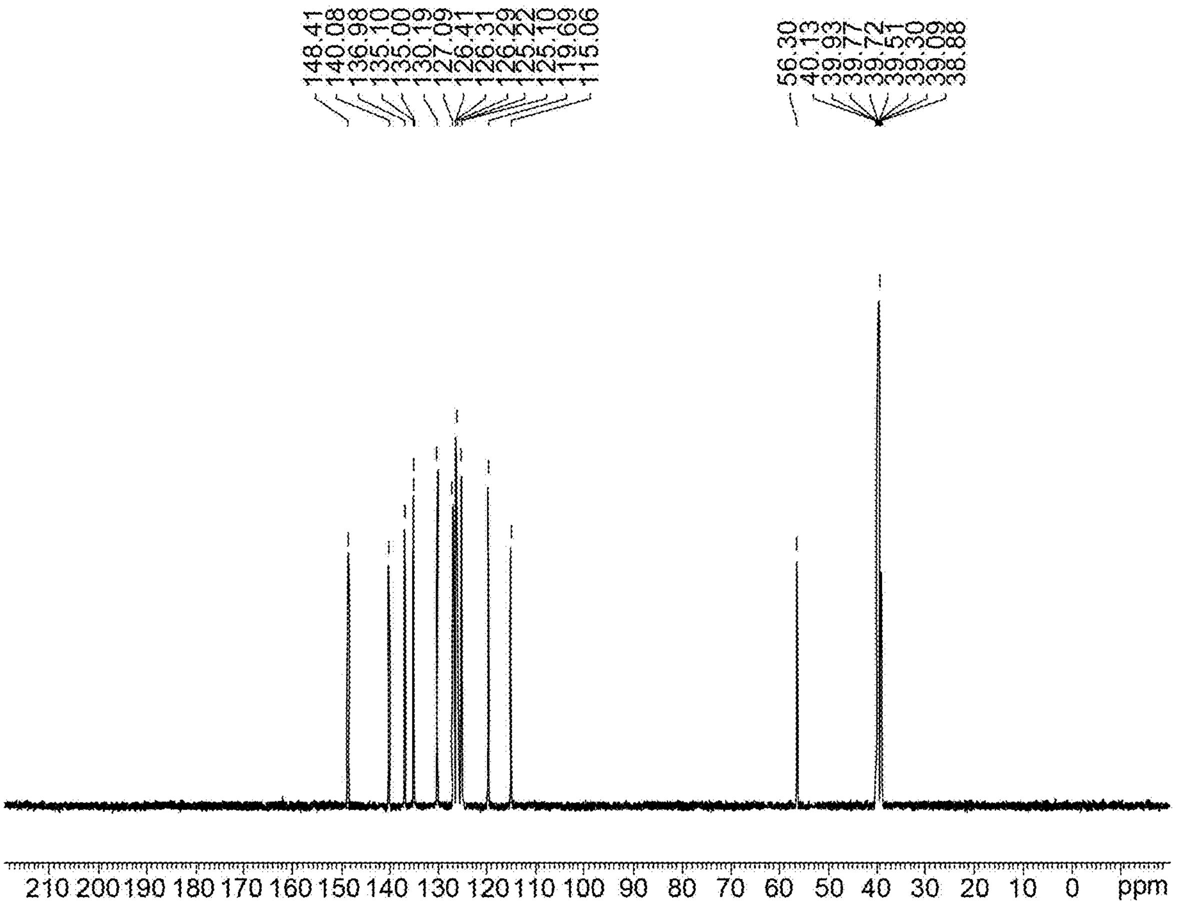
FIG. 4 shows a $^{13}C$ NMR spectrum of 9,9-bis(2-vinylbenzyl)-9H-fluorene prepared in Example 1.
Figure 5:
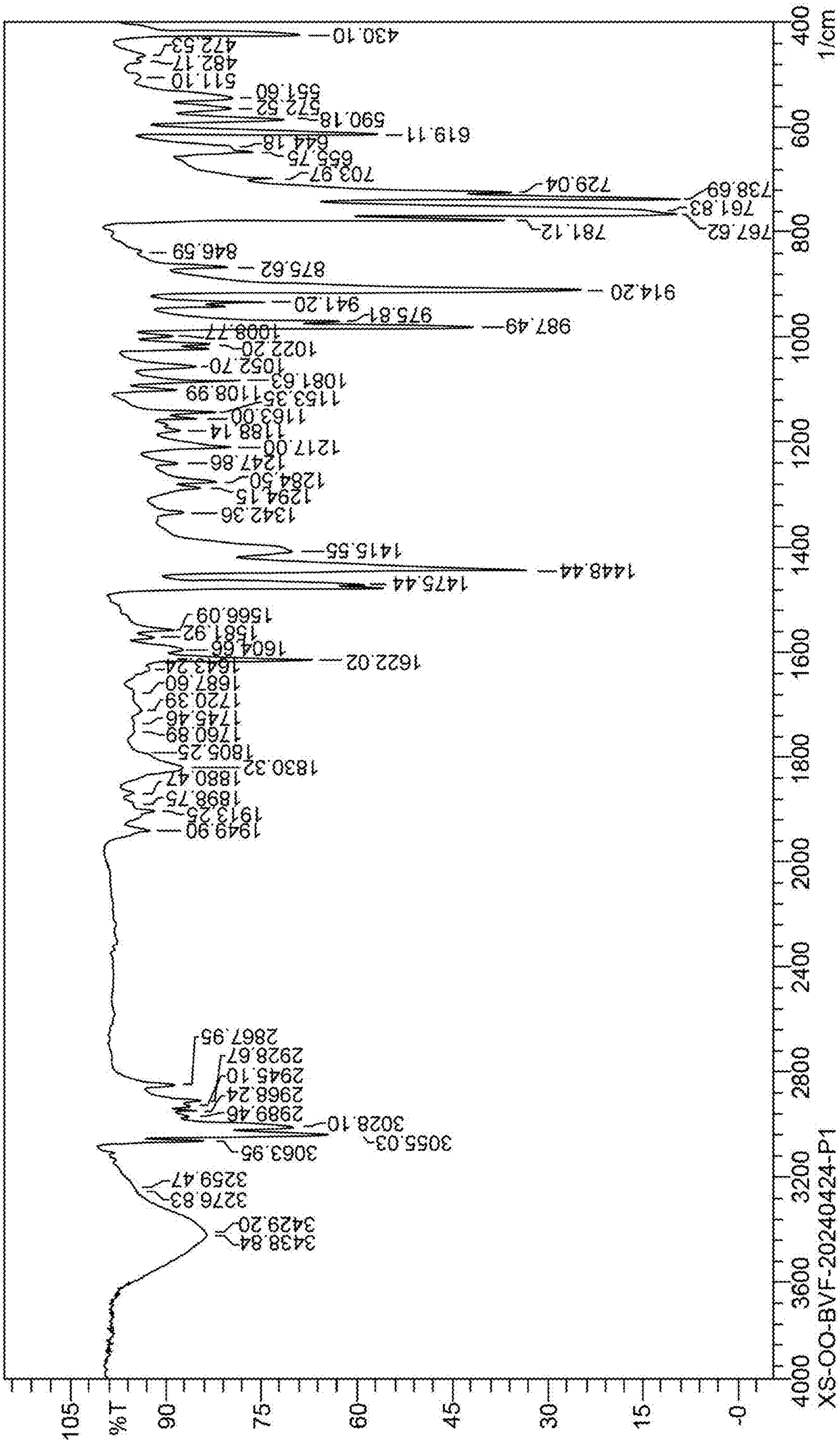
FIG. 5 shows an FT-IR spectrum of 9,9-bis(2-vinylbenzyl)-9H-fluorene prepared in Example 1.

FIG. 2 shows an $^{1}$H NMR spectrum of o,o-BVBF, FIG. 3 shows a two-dimensional diagram of a DQF-COSY $^{1}$H-$^{1}$H correlation nuclear magnetic resonance spectrum, FIG. 4 shows a $^{13}$C NMR spectrum of o,o-BVBF, and FIG. 5 shows an FT-JR spectrum of o,o-BVBF. $^{1}$H NMR (400 MHz, DMSO-$d_6$) δ: 3.54(s, 4H, 2×$CH_2$), 5.10(d, 2H, 2×ethylenic terminal hydrogen), 5.42 (d, 2H, 2×ethylenic terminal hydrogen), 6.54 (d, 2H, 2×hydrogen of benzene ring), 6.79-6.87(m, 4H, 2×hydrogen of benzene ring, 2×$CHCH_2$), 6.97-7.01(m, 2H, 2×hydrogen of benzene ring), 7.15-7.19(m 2H, 2×hydrogen of fluorene ring), 7.22-7.24 (in, 2H, 2×hydrogen of benzene ring), 7.25-7.29 (in, 2H, 2×hydrogen of fluorene ring), 7.40 (d, 2H, 2×hydrogen of fluorene ring), 7.60 (d, 2H, 2×hydrogen of fluorene ring). $^{13}$C NMR (100 MHz, DMSO-$d_6$) δ: 40.2($CH_2$), 56.3(9-fluorene C), 115.1, 119.7, 125.1, 125.2, 126.2, 126.3 126.4, 127.1, 130.2, 135.0, 135.1, 136.9, 140.1, 148.4 (C on benzene ring, C on fluorene ring, vinyl C.

Figure 7:
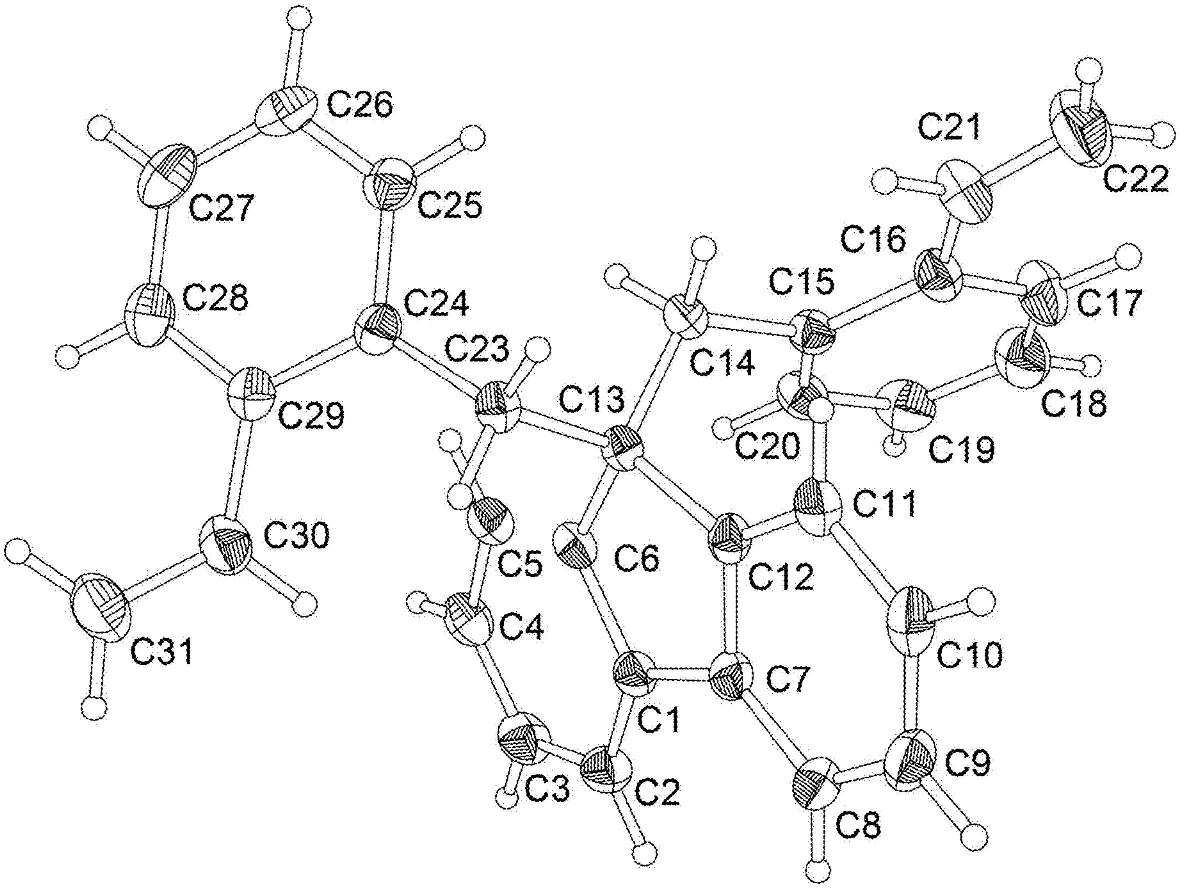
FIG. 7 shows a single-crystal structure of 9,9-bis(2-vinylbenzyl)-9H-fluorene prepared in Example 1.
Figure 8:
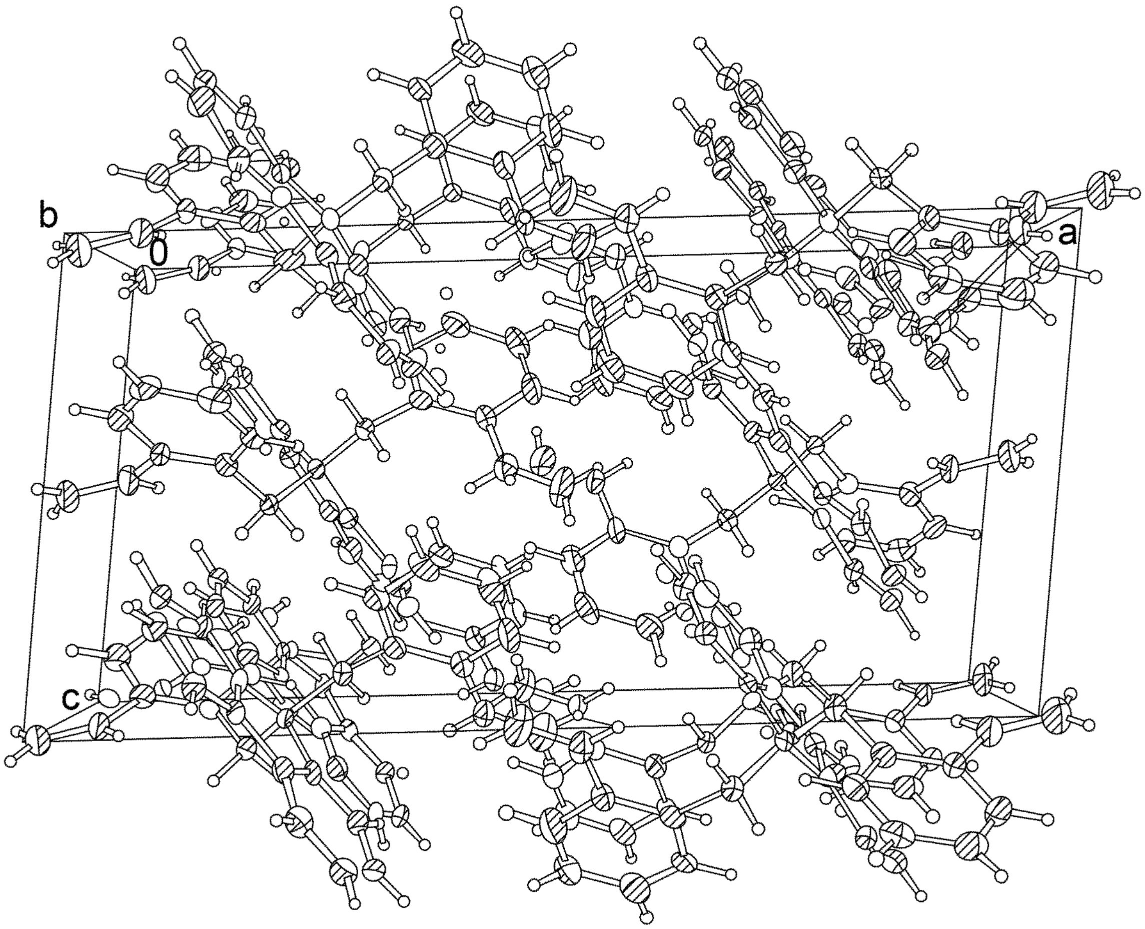
FIG. 8 shows a unit-cell stacking diagram of 9,9-bis(2-vinylbenzyl)-9H-fluorene prepared in Example 1.
Figure 9:
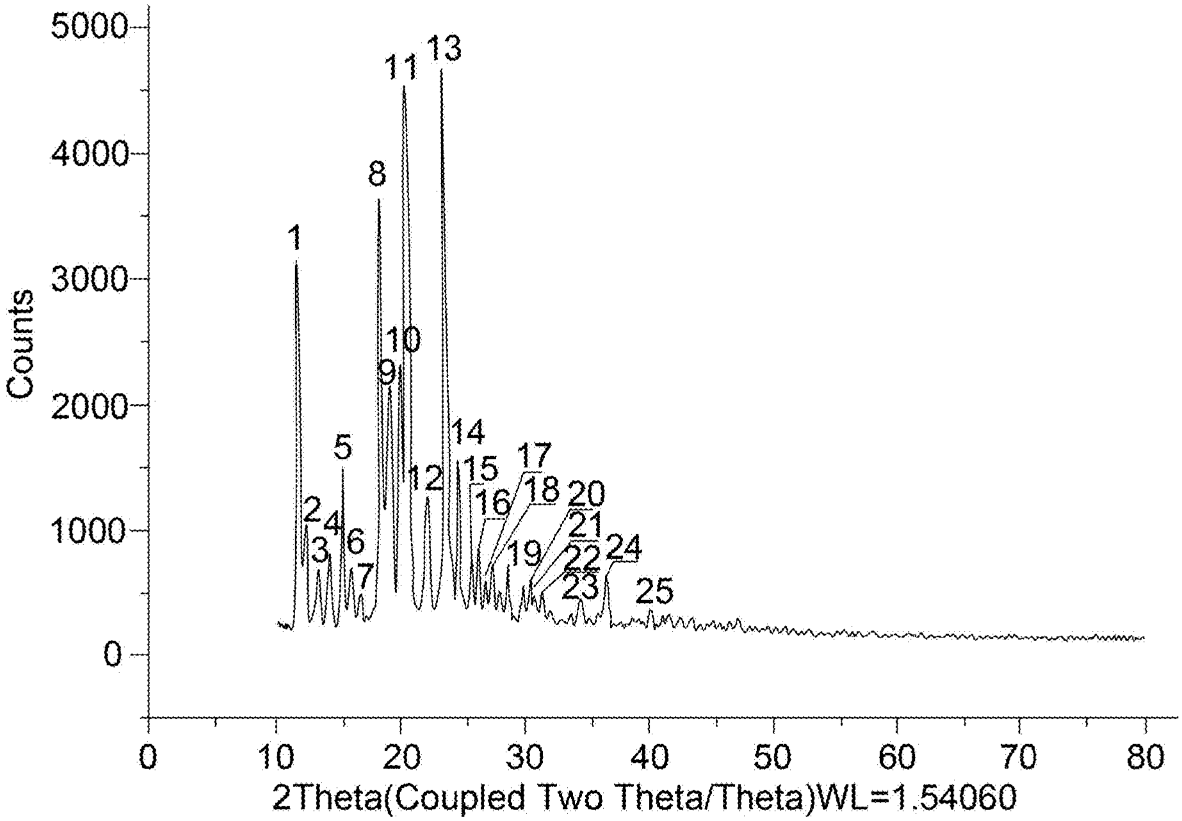
FIG. 9 shows a powder X-ray diffraction pattern of 9,9-bis(2-vinylbenzyl)-9H-fluorene prepared in Example 1.

FIG. 7 shows a single-crystal structure of o,o-BVBF, FIG. 8 shows a unit-cell stacking diagram of o,o-BVBF, and FIG. 9 shows a powder x-ray diffraction pattern of o,o-BVBF, where the crystallographic parameters of o,o-BVBF are shown in Tables 2-5. It can be seen that the single-crystal structure of o,o-BVBF is a white monoclinic crystal, and the 2θ characteristic peaks (relative intensity %) of powder x-ray diffraction analysis are as follows: 11.9 (70), 12.3 (20), 14.2 (20), 15.4 (30), 18.5 (76), 19.2 (44), 20.0 (47), 20.7 (100), 22.2 (21), 23.7 (100), 24.7 (30).

TABLE 2

Crystallography tables of o,o-BVBF and p,p-BVBF

| Compounds | o,o-BVBF | p,p-BVBF |
|---|---|---|
| Molecular formula | $C_{31}H_{26}$ | $C_{31}H_{26}$ |
| Molecular weight | 398.52 | 398.52 |
| Test temperature | 223.00 K | 223.00 K |
| Radiation source | CuKα | MoKα |
| Test wavelength | 1.54178 Å | 0.71073 Å |
| Crystal system | Monoclinic system | Triclinic system |
| Space group | $P2_1/c$ | $P\bar{1}$ |
| Unit-cell dimensions | a = 20.0139(5) Å, α = 90°<br>b = 10.9697(3) Å, β = 96.243(2)°<br>c = 10.1983(3) Å, γ = 90° | a = 10.6519(6) Å, α = 94.299(2)°<br>b = 14.6326(7) Å, β = 92.157(2)°<br>c = 14.7009(8) Å, γ = 91.265(3)° |
| Unit cell volume | 2225.72(11) $Å^3$ | 2282.6(2) $Å^3$ |
| Z | 4 | 4 |
| Density | 1.189 $Mg/m^3$ (megagram/cubic meter) | 1.160 $Mg/m^3$ |
| Absorption coefficient | 0.504 $mm^{-1}$ | 0.065 $mm^{-1}$ |
| F(000) | 848.0 | 848.0 |
| Crystal size | 0.12 × 0.11 × 0.10 $mm^3$ | 0.13 × 0.11 × 0.10 $mm^3$ |
| Range of Θ | 2.221-68.346° | 2.321-27.495° |
| Index range | −23 <= h <= 24, 13 <= k <= 13, −12 <= l <= 12 | −13 <= h <= 13, −18 <= k <= 18, −19 <= l <= 19 |
| Number of collected diffraction points | 28219 | 60205 |
| Number of independent diffraction points | 4057[R(int) = 0.0672] | 10425[R(int) = 0.0826] |
| Θ = 68.346° integrity | 99.6% | 99.8% |
| Absorption correction | Semi-empirical from equivalents | Semi-empirical from equivalents |
| Maximum and minimum transmittance | 0.753 and 0.674 | 0.743 and 0.712 |
| Refining method | Full-matrix least-squares on $F^2$ | Full-matrix least-squares on $F^2$ |
| Number of data points/number of limitations added/number of refined parameters | 4057/0/280 | 10425/234/704 |
| GooF value | 1.048 | 1.036 |
| Deviation factor [I > 2sigma(I)] | $R_1$ = 0.0400, $wR_2$ = 0.1011 | $R_1$ = 0.0527, $wR_2$ = 0.1259 |
| Deviation factor (alldata) | $R_1$ = 0.0606, $wR_2$ = 0.1072 | $R_1$ = 0.0927, $wR_2$ = 0.1544 |
| Residual electron cloud density | 0.12 and −0.15e · $Å^{-3}$ | 0.56 and −0.24e · $Å^{-3}$ |

TABLE 3

Atomic coordinates (×$10^4$) of o,o-BVBF and equivalent isotropic displacement parameters ($Å^2$ × $10^3$)

| | X | Y | Z | U(eq) |
|---|---|---|---|---|
| C(1) | 2130.2(6) | 4152.1(11) | 4446.8(13) | 37.1(3) |
| C(2) | 1756.6(7) | 3194.1(13) | 3857.6(16) | 48.5(3) |
| C(3) | 1337.1(7) | 3419.2(14) | 2710.8(16) | 53.0(4) |
| C(4) | 1282.2(6) | 4580.5(14) | 2170.1(15) | 47.6(3) |
| C(5) | 1644.9(6) | 5546.7(13) | 2778.3(13) | 39.9(3) |
| C(6) | 2073.3(5) | 5328.3(11) | 3911.5(12) | 34.1(3) |
| C(7) | 2627.0(6) | 4171.2(12) | 5610.1(13) | 37.7(3) |
| C(8) | 2847.6(7) | 3251.1(13) | 6491.0(15) | 48.3(3) |

TABLE 3-continued

| Atomic coordinates (×10⁴) of o,o-BVBF and equivalent isotropic displacement parameters ($Å^2 \times 10^3$) | | | | |
|---|---|---|---|---|
| | X | Y | Z | U(eq) |
| C(9) | 3319.3(7) | 3530.3(15) | 7544.4(16) | 54.4(4) |
| C(10) | 3572.6(6) | 4703.0(15) | 7707.1(14) | 48.3(4) |
| C(11) | 3358.3(6) | 5627.7(13) | 6823.5(13) | 40.1(3) |
| C(12) | 2880.5(5) | 5358.4(11) | 5777.7(12) | 34.1(3) |
| C(13) | 2531.3(5) | 6208.6(11) | 4736.9(11) | 32.1(3) |
| C(14) | 3025.2(6) | 6903.6(11) | 3932.3(12) | 34.8(3) |
| C(15) | 3556.7(6) | 6156.6(12) | 3347.6(12) | 36.9(3) |
| C(16) | 4248.1(6) | 6294.1(13) | 3772.9(14) | 44.9(3) |
| C(17) | 4705.7(7) | 5587.9(17) | 3154.5(18) | 63.0(5) |
| C(18) | 4504.8(8) | 4799.9(17) | 2151(2) | 67.1(5) |
| C(19) | 3830.5(8) | 4682.2(15) | 1712.0(17) | 56.6(4) |
| C(20) | 3365.3(7) | 5358.7(13) | 2313.2(14) | 44.9(3) |
| C(21) | 4504.3(7) | 7151.0(16) | 4820.0(16) | 55.1(4) |
| C(22) | 5117.3(9) | 7358(2) | 5263(2) | 83.2(6) |
| C(23) | 2119.2(6) | 7164.0(12) | 5460.6(12) | 35.7(3) |
| C(24) | 1681.8(6) | 8046.8(11) | 4612.1(12) | 36.1(3) |
| C(25) | 1972.2(7) | 9076.6(12) | 4108.9(13) | 42.4(3) |
| C(26) | 1602.1(8) | 9922.0(13) | 3338.6(15) | 51.3(4) |
| C(27) | 917.6(9) | 9774.0(15) | 3078.8(16) | 59.3(4) |
| C(28) | 614.0(7) | 8783.2(15) | 3588.2(16) | 54.8(4) |
| C(29) | 980.6(6) | 7905.7(13) | 4357.7(13) | 42.3(3) |
| C(30) | 622.3(7) | 6863.4(15) | 4877.3(16) | 52.3(4) |
| C(31) | −0.4(8) | 6869(2) | 5148(2) | 72.9(5) |

TABLE 4

| Bond length [Å] and bond angle [°] of o,o-BVBF | | | | | |
|---|---|---|---|---|---|
| C(1)-C(2) | 1.3881(19) | C(25)-C(26) | 1.378(2) | C(12)-C(13)-C(14) | 113.49(9) |
| C(1)-C(6) | 1.4008(18) | C(26)-C(27) | 1.376(2) | C(12)-C(13)-C(23) | 107.82(9) |
| C(1)-C(7) | 1.4628(19) | C(27)-C(28) | 1.374(2) | C(14)-C(13)-C(23) | 108.57(10) |
| C(2)-C(3) | 1.386(2) | C(28)-C(29) | 1.398(2) | C(15)-C(14)-C(13) | 117.20(10) |
| C(3)-C(4) | 1.388(2) | C(29)-C(30) | 1.478(2) | C(16)-C(15)-C(14) | 121.84(12) |
| C(4)-C(5) | 1.3918(19) | C(30)-C(31) | 1.305(2) | C(20)-C(15)-C(14) | 119.41(11) |
| C(5)-C(6) | 1.3830(18) | C(2)-C(1)-C(6) | 120.76(13) | C(20)-C(15)-C(16) | 118.66(12) |
| C(6)-C(13) | 1.5210(16) | C(2)-C(1)-C(7) | 130.43(13) | C(15)-C(16)-C(21) | 122.90(12) |
| C(7)-C(8) | 1.3909(19) | C(6)-C(1)-C(7) | 108.79(11) | C(17)-C(16)-C(15) | 117.99(14) |
| C(7)-C(12) | 1.4014(18) | C(3)-C(2)-C(1) | 118.61(14) | C(17)-C(16)-C(21) | 119.10(13) |
| C(8)-C(9) | 1.385(2) | C(2)-C(3)-C(4) | 120.90(13) | C(18)-C(17)-C(16) | 122.25(15) |
| C(9)-C(10) | 1.386(2) | C(3)-C(4)-C(5) | 120.47(14) | C(17)-C(18)-C(19) | 119.96(14) |
| C(10)-C(11) | 1.393(2) | C(6)-C(5)-C(4) | 119.10(13) | C(18)-C(19)-C(20) | 119.14(15) |
| C(11)-C(12) | 1.3847(18) | C(1)-C(6)-C(13) | 110.52(11) | C(19)-C(20)-C(15) | 121.97(13) |
| C(12)-C(13) | 1.5243(17) | C(5)-C(6)-C(1) | 120.13(12) | C(22)-C(21)-C(16) | 127.86(16) |
| C(13)-C(14) | 1.5518(15) | C(5)-C(6)-C(13) | 129.35(11) | C(24)-C(23)-C(13) | 117.40(10) |
| C(13)-C(23) | 1.5671(16) | C(8)-C(7)-C(1) | 130.80(13) | C(25)-C(24)-C(23) | 119.40(11) |
| C(14)-C(15) | 1.5154(16) | C(8)-C(7)-C(12) | 120.68(13) | C(25)-C(24)-C(29) | 117.95(12) |
| C(15)-C(16) | 1.4124(18) | C(12)-C(7)-C(1) | 108.51(11) | C(29)-C(24)-C(23) | 122.58(11) |
| C(15)-C(20) | 1.3921(19) | C(9)-C(8)-C(7) | 118.83(14) | C(26)-C(25)-C(24) | 122.38(13) |
| C(16)-C(17) | 1.401(2) | C(8)-C(9)-C(10) | 120.51(14) | C(27)-C(26)-C(25) | 119.50(14) |
| C(16)-C(21) | 1.472(2) | C(9)-C(10)-C(11) | 121.04(14) | C(28)-C(27)-C(26) | 119.49(14) |
| C(17)-C(18) | 1.367(3) | C(12)-C(11)-C(10) | 118.76(13) | C(27)-C(28)-C(29) | 122.00(14) |
| C(18)-C(19) | 1.381(2) | C(7)-C(12)-C(13) | 110.56(10) | C(24)-C(29)-C(30) | 122.12(12) |
| C(19)-C(20) | 1.385(2) | C(11)-C(12)-C(7) | 120.18(12) | C(28)-C(29)-C(24) | 118.65(13) |
| C(21)-C(22) | 1.281(2) | C(11)-C(12)-C(13) | 129.18(12) | C(28)-C(29)-C(30) | 119.23(13) |
| C(23)-C(24) | 1.5128(17) | C(6)-C(13)-C(12) | 101.54(10) | C(31)-C(30)-C(29) | 125.71(16) |

TABLE 4-continued

| Bond length [Å] and bond angle [°] of o,o-BVBF | | | |
|---|---|---|---|
| C(24)-C(25) | 1.3936 (18) | C(6)-C(13)-C(14) | 113.55 (10) |
| C(24)-C(29) | 1.4076 (18) | C(6)-C(13)-C(23) | 111.65 (9) |

TABLE 5

| Anisotropic displacement parameters ($Å^2 \times 10^3$) of o,o-BVBF | | | | | | |
|---|---|---|---|---|---|---|
| C(1) | 32.3(6) | 38.2(7) | 41.9(7) | −2.0(5) | 9.2(5) | 0.6(5) |
| C(2) | 45.7(7) | 38.1(7) | 62.0(9) | −4.6(6) | 7.3(6) | −4.6(5) |
| C(3) | 46.3(7) | 49.8(9) | 62.0(9) | −14.2(7) | 2.4(7) | −11.1(6) |
| C(4) | 37.6(6) | 59.8(9) | 44.4(8) | −6.0(6) | 0.3(6) | −8.7(6) |
| C(5) | 33.9(6) | 47.4(7) | 38.2(7) | 0.7(5) | 2.4(5) | −4.8(5) |
| C(6) | 28.8(5) | 39.2(7) | 35.1(6) | −2.4(5) | 7.2(5) | −2.5(4) |
| C(7) | 32.7(6) | 40.2(7) | 41.4(7) | 2.2(5) | 10.1(5) | 5.6(5) |
| C(8) | 43.2(7) | 43.3(8) | 59.4(9) | 10.1(6) | 9.5(6) | 9.1(6) |
| C(9) | 45.4(7) | 62.3(10) | 55.7(9) | 19.2(7) | 5.5(7) | 17.0(7) |
| C(10) | 35.3(6) | 68.1(10) | 41.0(8) | 4.4(7) | 1.8(6) | 12.5(6) |
| C(11) | 31.5(6) | 50.5(8) | 38.4(7) | −0.7(6) | 4.3(5) | 5.7(5) |
| C(12) | 28.6(5) | 40.9(7) | 33.7(6) | 0.9(5) | 7.8(5) | 4.8(5) |
| C(13) | 28.6(5) | 36.3(6) | 31.2(6) | −0.4(5) | 2.4(4) | −0.1(4) |
| C(14) | 31.2(5) | 36.9(6) | 36.3(6) | 0.2(5) | 4.0(5) | −2.1(5) |
| C(15) | 35.2(6) | 40.2(7) | 36.4(6) | 3.3(5) | 8.2(5) | −1.8(5) |
| C(16) | 35.5(6) | 52.8(8) | 47.5(8) | 1.6(6) | 9.0(6) | −1.2(5) |
| C(17) | 37.3(7) | 79.5(12) | 74.5(12) | −7.2(9) | 15.5(7) | 5.4(7) |
| C(18) | 55.1(9) | 70.8(11) | 80.4(12) | −12.9(9) | 30.1(9) | 7.9(8) |
| C(19) | 62.7(9) | 55.0(9) | 55.6(9) | −13.0(7) | 22.7(8) | −5.7(7) |
| C(20) | 43.0(7) | 49.6(8) | 43.2(7) | −3.0(6) | 10.1(6) | −4.5(6) |
| C(21) | 37.2(7) | 71.3(10) | 56.9(9) | −6.2(8) | 5.0(6) | −7.4(6) |
| C(22) | 46.6(9) | 91.6(15) | 108.3(17) | −26.5(13) | −6.0(9) | −7.8(9) |
| C(23) | 32.9(5) | 41.2(7) | 33.1(6) | −0.2(5) | 3.8(5) | 2.6(5) |
| C(24) | 38.1(6) | 37.8(7) | 32.8(6) | −1.8(5) | 5.8(5) | 4.4(5) |
| C(25) | 47.0(7) | 37.6(7) | 43.6(7) | −4.4(5) | 10.1(6) | 1.1(5) |
| C(26) | 73.3(9) | 35.3(7) | 46.8(8) | 1.2(6) | 13.9(7) | 5.5(6) |
| C(27) | 74.4(10) | 51.0(9) | 50.9(9) | 8.2(7) | −0.7(8) | 18.9(7) |
| C(28) | 45.0(7) | 62.3(10) | 55.0(9) | 3.1(7) | −4.2(6) | 12.1(7) |
| C(29) | 38.2(6) | 47.1(7) | 41.4(7) | 0.4(6) | 3.2(5) | 5.9(5) |
| C(30) | 37.8(7) | 59.5(9) | 59.6(9) | 6.7(7) | 4.4(6) | 0.3(6) |
| C(31) | 45.1(8) | 94.9(14) | 79.6(13) | 17.4(10) | 11.1(8) | −2.8(8) |

Example 2

500 mL of acetonitrile, 1.4 mol of potassium t-butoxide, 30 g of PEG-400, and 0.5 g of polymerization inhibitor 701 were added to a reaction flask, and 0.6 mol of fluorene and 1.4 mol of 2-vinylbenzyl chloride (HPLC, 99%) were then added thereto while stirring. At a temperature of 30-35° C. and a stirring speed of 350 r/min, the resulting mixture was subjected to reaction until the content of fluorene was lower than 1 wt % according to HPLC analysis. The reaction was stopped, and acetonitrile was distilled off. 500 mL of water and 500 mL of toluene were added thereto for layering. The organic phase was washed with a saturated ammonium chloride solution, and washed with water for 3 times (500 mL of water for each time) until neutral. Toluene was distilled off under reduced pressure, and a mixed solvent of toluene and methanol in a volume ratio of 1:0.3 was added thereto. The resulting mixture was heated until being fully dissolved, and cooled at a cooling rate of 0.5° C./min to 5° C. for crystallization at constant temperature. The resulting system was then filtered, and the resulting solid component was dried at 90° C. to constant weight so as to obtain 199.5 g of a 9,9-bis(2-vinylbenzyl)-9H-fluorene which was a white crystal with an HPLC purity of 99.5%, with a yield of 83.5%.

Example 3

Figure 10:
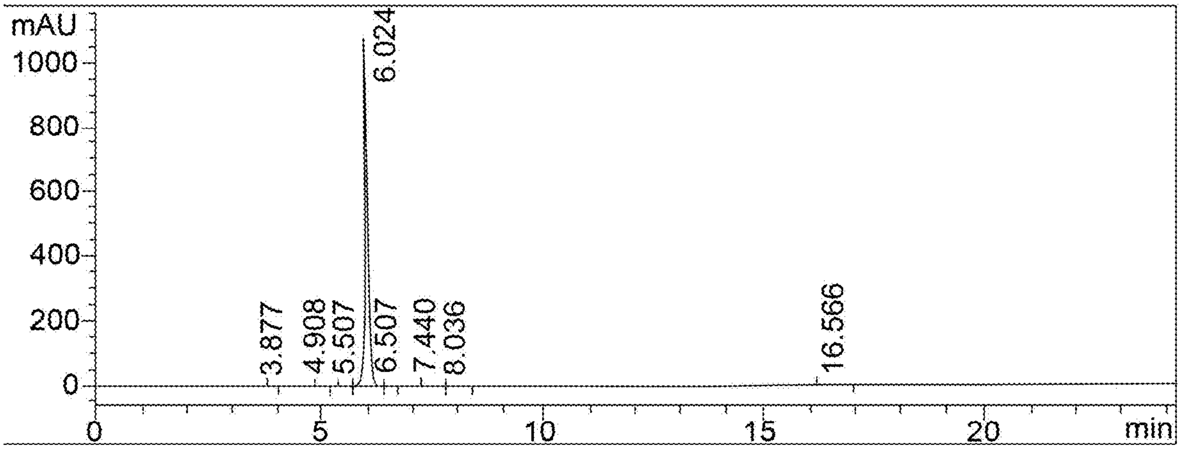
FIG. 10 shows an HPLC spectrum of 9,9-bis(4-vinylbenzyl)-9H-fluorene prepared in Example 3.
Figure 13:
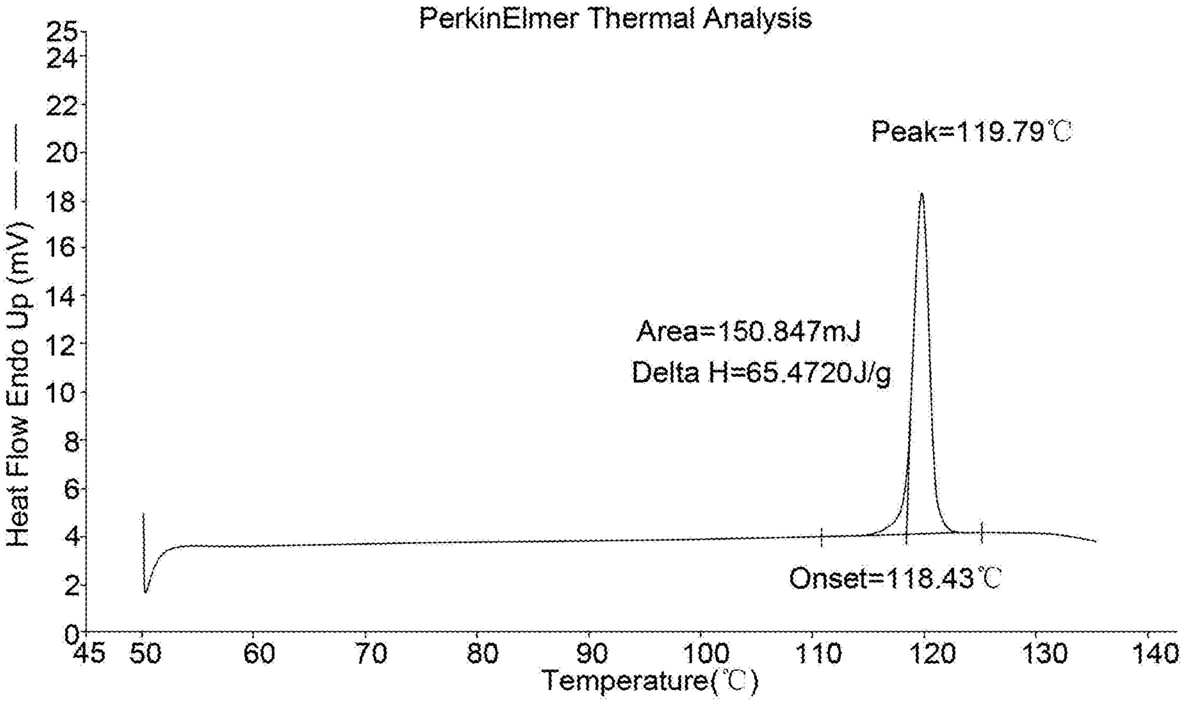
FIG. 13 shows a DSC spectrum of a thermoanalysis of 9,9-bis(4-vinylbenzyl)-9H-fluorene prepared in Example 3.

350 mL of acetonitrile, 1.4 mol of potassium hydroxide powder, 30 g of PEG-400, and 0.5 g of polymerization inhibitor 701 were added to a reaction flask, and 0.6 mol of fluorene and 1.4 mol of 4-vinylbenzyl chloride (HPLC, 99.5%) were then added while stirring. At a temperature of 30-35° C. and a stirring speed of 350 r/min, the resulting mixture was subjected to reaction until the content of fluorene was lower than 1 wt % according to HPLC analysis. The reaction was stopped, and acetonitrile was distilled off. 500 mL of water and 500 mL of toluene were then added for layering. The organic phase was washed with a saturated ammonium chloride solution, and washed with water for 3 times (500 mL of water for each time) until neutral. Toluene was distilled off under reduced pressure, and a mixed solvent of toluene and methanol in a volume ratio of 1:0.3 was added thereto. The resulting mixture was heated until being fully dissolved, and cooled at a cooling rate of 0.5° C./min to 5° C. for crystallization at constant temperature. The resulting system was filtered, and the resulting solid component was dried at 90° C. to constant weight so as to obtain 197.6 g of a 9,9-bis(4-vinylbenzyl)-9H-fluorene, i.e., p,p-BVBF which was a white crystal having an HPLC purity (FIG. 10 and Table 6) of 99.7%, a melting point of 118.4-119.8° C. (thermal analysis DSC melting absorption peak, FIG. 13), with a yield of 82.6%.

TABLE 6

| HPLC peak information of p,p-BVBF | | | | | | |
|---|---|---|---|---|---|---|
| Peak | Retention time (min) | Type | Peak width (min) | Peak area (mAU · s) | Peak height (mAU) | Peak area (%) |
| 1 | 3.877 | BV | 0.0959 | 1.13256 | 0.182081 | 0.0140 |
| 2 | 4.908 | VB | 0.1015 | 2.72516 | 0.406471 | 0.0338 |
| 3 | 5.507 | BB | 0.1120 | 3.14688 | 0.428014 | 0.0390 |
| 4 | 6.024 | BV | 0.1122 | 8043.53857 | 1110.62878 | 99.7056 |
| 5 | 6.507 | VB | 0.1244 | 3.88065 | 0.461084 | 0.0481 |
| 6 | 7.440 | BV | 0.2139 | 2.31902 | 0.147576 | 0.0287 |
| 7 | 8.036 | VB | 0.1490 | 9.18154 | 0.939460 | 0.1138 |
| 8 | 16.566 | BB | 0.2406 | 1.36443 | 0.0691055 | 0.0169 |

Figure 11:
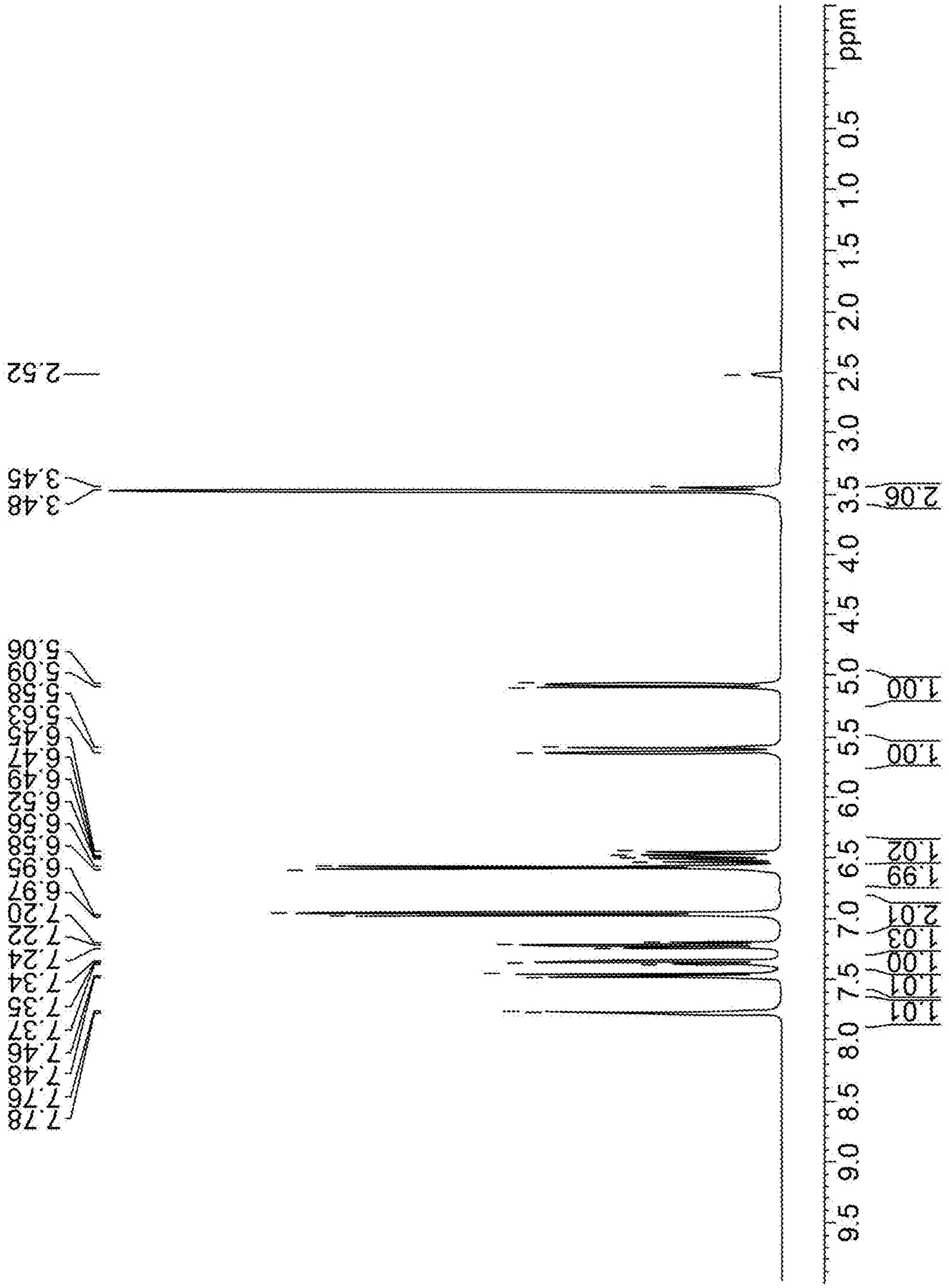
FIG. 11 shows an $^{1}H$ NMR spectrum of 9,9-bis(4-vinylbenzyl)-9H-fluorene prepared in Example 3.
Figure 12:
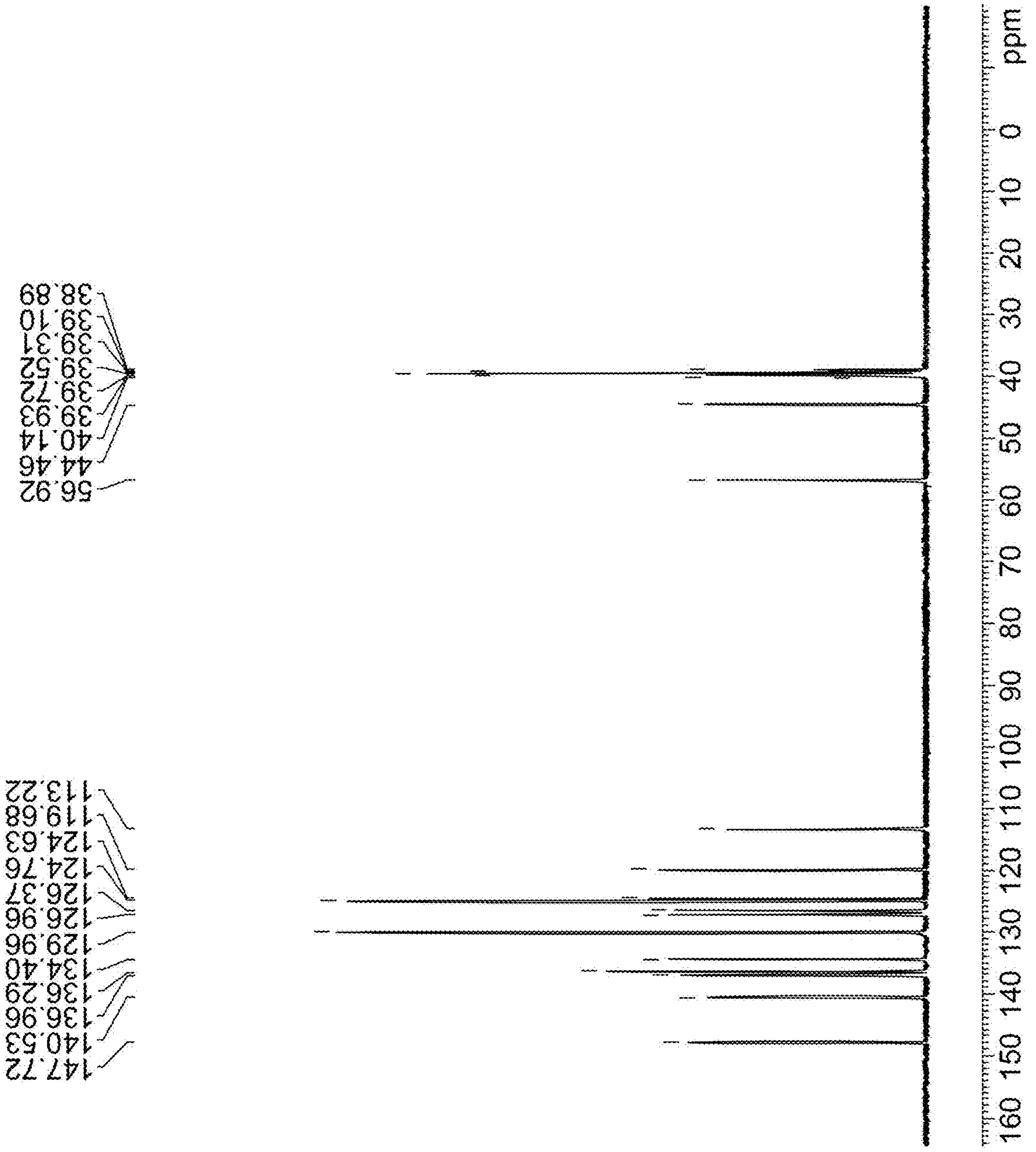
FIG. 12 shows a $^{13}C$NMR spectrum of 9,9-bis(4-vinylbenzyl)-9H-fluorene prepared in Example 3.
Figure 14:
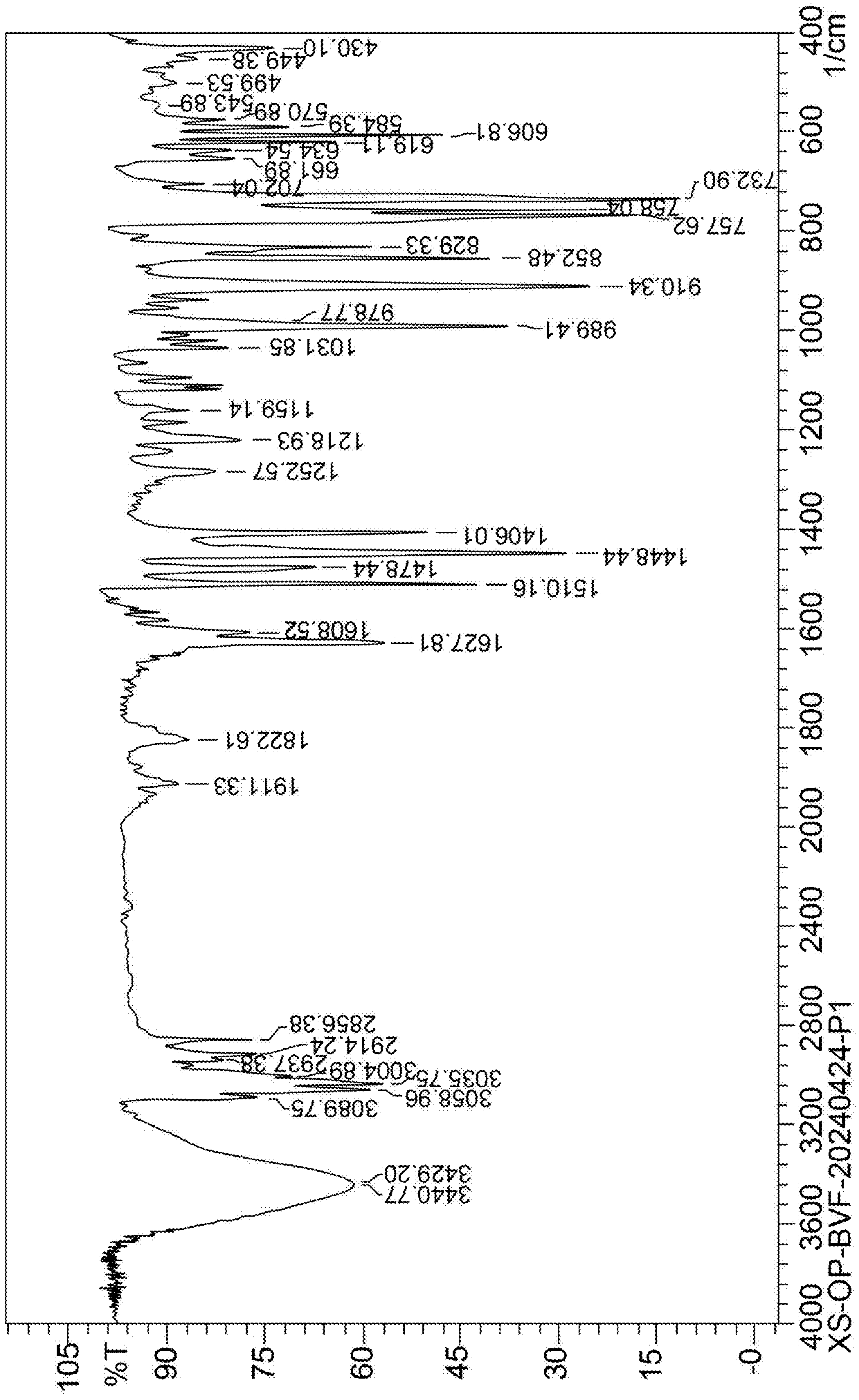
FIG. 14 shows an fourier-transform infrared (FT-IR) spectrum of 9,9-bis(4-vinylbenzyl)-9H-fluorene prepared in Example 3.

FIG. 11 shows an $^1H$ NMR spectrum of p,p-BVBF, FIG. 12 shows a $^{13}C$ NMR spectrum of p,p-BVBF, and FIG. 14 shows an FT-JR spectrum of p,p-BVBF. $^1H$ NMR (400 MHz, DMSO-$d_6$) δ: 3.48(s, 4H, 2×$CH_2$), 5.08(d, 2H, 2×ethylenic terminal hydrogen) 5.61 (d, 2H, 2×ethylenic terminal hydrogen), 6.45-6.52 (in, 2H, 2×$CH{=}CH_2$), 6.57 (d, 4H, 4×hydrogen of benzene ring), 6.96 (d, 4H, 4×hydrogen of benzene ring), 7.20-7.24 (in, 2H, 2×hydrogen of fluorene ring), 7.34-7.37 (n, 2H, 2×hydrogen of fluorene ring), 7.47 (d, 2H, 2×hydrogen of fluorene ring), 7.77 (d, 2H, 2×hydrogen of fluorene ring). $^{13}C$ NMR (100 MHz, DMSO-$d_6$) δ:44.5 ($CH_2$), 56.9 (9-fluorene C), 113.2, 119.7, 124.6 124.8, 126.4, 126.9, 129.9 134.4, 136.3, 136.9, 140.5, 147.7 (C on benzene ring, C on fluorene ring, vinyl C).

Figure 15:
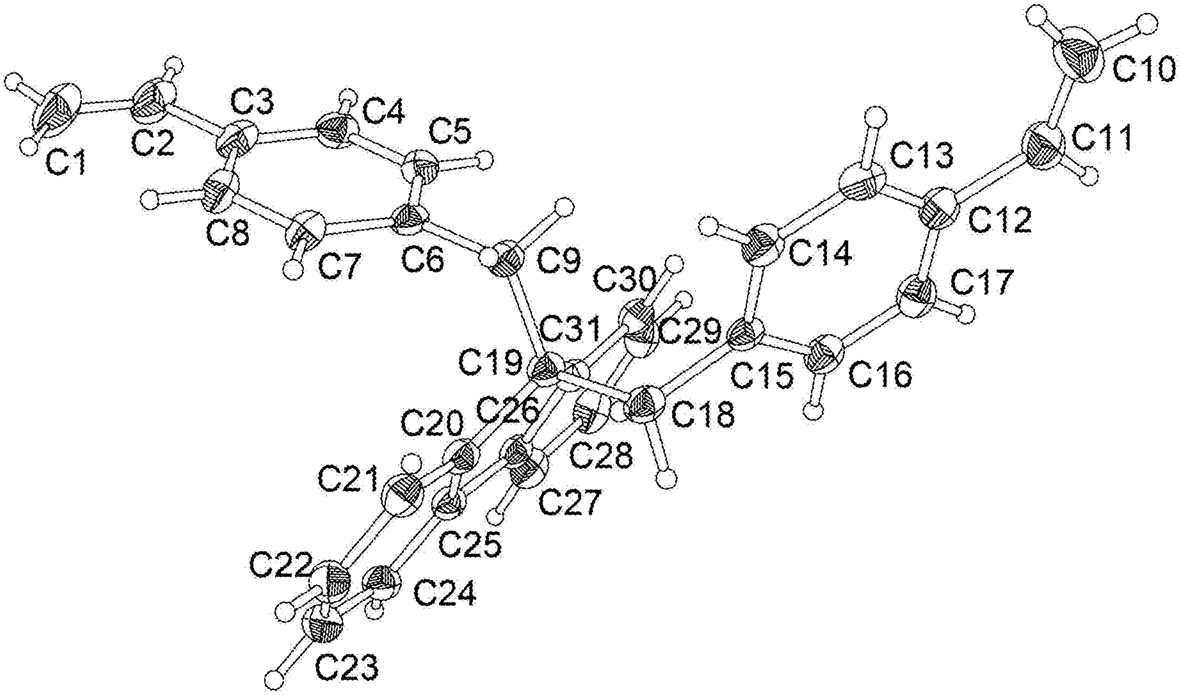
FIG. 15 shows a single-crystal structure of 9,9-bis(4-vinylbenzyl)-9H-fluorene prepared in Example 3.
Figure 16:
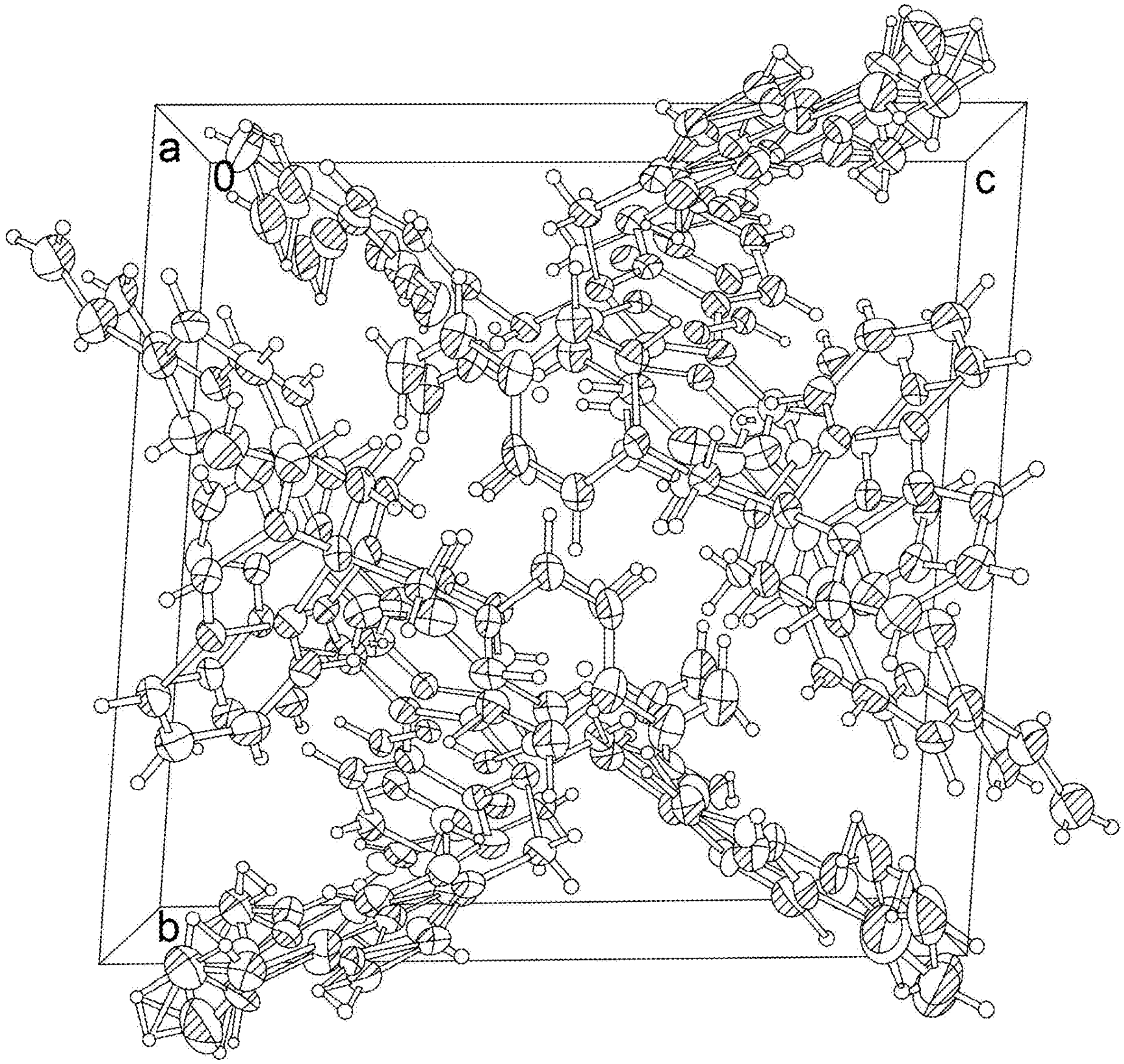
FIG. 16 shows a unit-cell stacking diagram of 9,9-bis(4-vinylbenzyl)-9H-fluorene prepared in Example 3.
Figure 17:
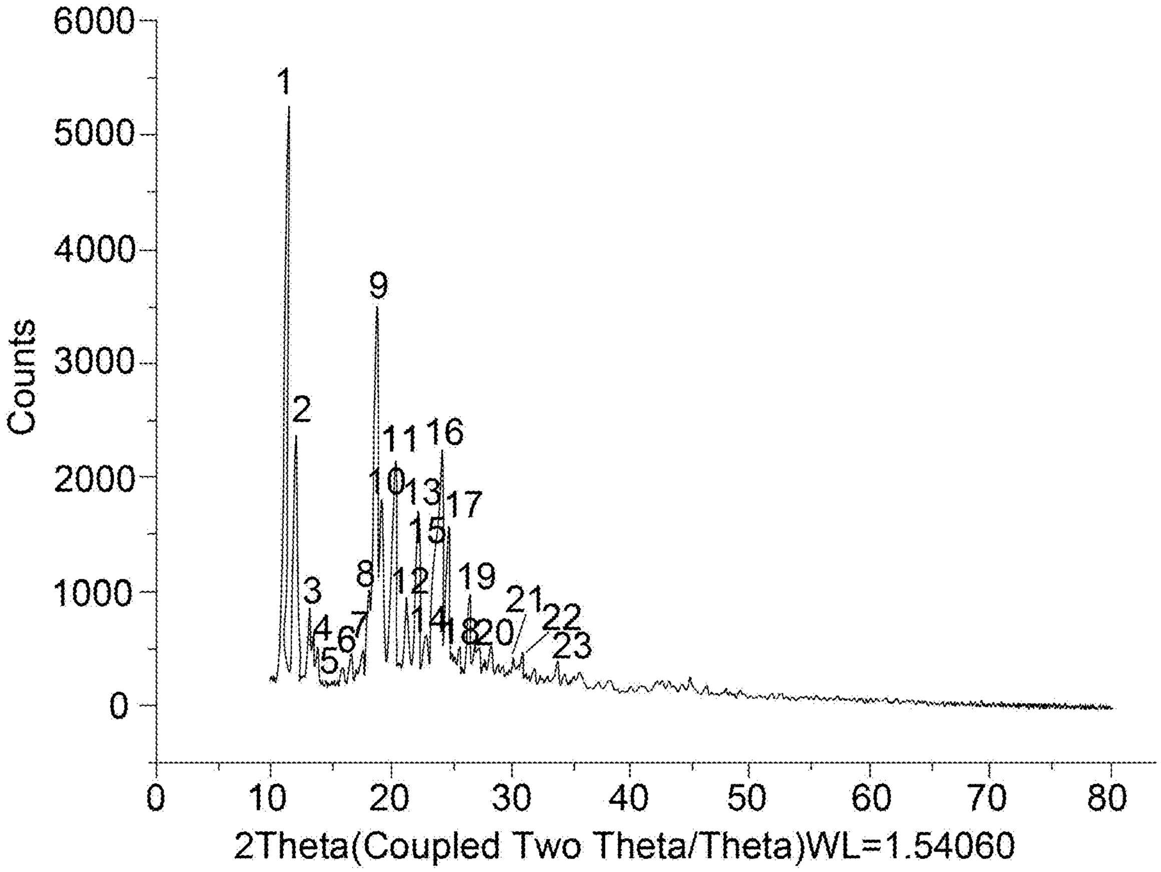
FIG. 17 shows a powder X-ray diffraction pattern of 9,9-bis(4-vinylbenzyl)-9H-fluorene prepared in Example 3.

FIG. 15 shows a single-crystal structure of p,p-BVBF, FIG. 16 shows a unit-cell stacking diagram of p,p-BVBF, and FIG. 17 shows a powder x-ray diffraction pattern of p,p-BVBF, where the crystallographic parameters of p,p-BVBF are shown in Table 2 and Tables 7-9. It can be seen that the single-crystal structure of p,p-BVBF is a white triclinic crystal, and the 2θ characteristic peaks of powder x-ray diffraction analysis (relative intensity %) are as follows: 11.1(100), 12.0(43), 18.6(64), 19.1(30), 20.0(36), 22.1 (29), 23.6(25), 24.0(39), 24.6(26).

TABLE 7

| Atomic coordinates (×10$^4$) of p,p-BVBF and equivalent isotropic displacement parameters (Å$^2$ × 10$^3$) | | | | |
|---|---|---|---|---|
| | x | y | z | U(eq) |
| C(1) | 1618(3) | 8186(2) | 10925.0(18) | 114.2(11) |
| C(2) | 1172(3) | 7479.9(19) | 10444.7(17) | 90.8(8) |
| C(3) | 1698(2) | 6996.7(14) | 9634.0(14) | 63.7(5) |
| C(4) | 1142.9(19) | 6185.7(16) | 9253.7(15) | 67.7(6) |
| C(5) | 1627.8(18) | 5710.9(14) | 8504.0(14) | 60.8(5) |
| C(6) | 2686.2(17) | 6028.3(12) | 8097.0(11) | 49.1(4) |
| C(7) | 3249(2) | 6839.2(12) | 8478.9(13) | 56.6(5) |
| C(8) | 2764(2) | 7315.4(13) | 9229.0(13) | 64.2(5) |
| C(9) | 3179.0(18) | 5544.1(12) | 7243.3(11) | 52.3(4) |
| C(10) | 390(3) | 3061(3) | 3070.2(18) | 108.4(10) |
| C(11) | 1088(2) | 2722(2) | 3643.7(16) | 82.5(7) |
| C(12) | 1977(2) | 3192.4(17) | 4352.2(14) | 67.6(5) |
| C(13) | 2235(2) | 4130.5(16) | 4416.0(13) | 68.2(5) |
| C(14) | 3073(2) | 4536.8(14) | 5094.9(12) | 60.7(5) |
| C(15) | 3665.4(17) | 4009.5(12) | 5717.6(11) | 48.2(4) |
| C(16) | 3395.1(19) | 3074.9(13) | 5632.8(12) | 56.4(5) |
| C(17) | 2579(2) | 2678.9(15) | 4966.7(14) | 63.4(5) |
| C(18) | 4611.5(17) | 4413.6(13) | 6432.3(12) | 53.1(4) |
| C(19) | 4121.5(16) | 4773.2(12) | 7379.9(11) | 47.6(4) |
| C(20) | 5263.5(17) | 5092.4(12) | 7981.7(12) | 48.7(4) |
| C(21) | 6149.0(19) | 5769.8(14) | 7854.0(14) | 60.9(5) |
| C(22) | 7153(2) | 5916.4(15) | 8485.0(15) | 68.8(6) |
| C(23) | 7268(2) | 5390.8(16) | 9223.2(14) | 69.3(6) |
| C(24) | 6395.8(19) | 4712.1(14) | 9354.4(13) | 60.1(5) |
| C(25) | 5392.2(17) | 4561.8(12) | 8728.0(11) | 49.6(4) |

TABLE 7-continued

| Atomic coordinates (×10$^4$) of p,p-BVBF and equivalent isotropic displacement parameters (Å$^2$ × 10$^3$) | | | | |
|---|---|---|---|---|
| | x | y | z | U(eq) |
| C(26) | 4353.1(17) | 3889.1(12) | 8683.5(11) | 49.1(4) |
| C(27) | 4053(2) | 3213.2(14) | 9266.7(13) | 63.2(5) |
| C(28) | 2983(2) | 2677.5(15) | 9074.8(15) | 71.8(6) |
| C(29) | 2212(2) | 2806.7(14) | 8322.3(14) | 67.3(6) |
| C(30) | 2512.4(18) | 3468.9(13) | 7733.4(13) | 56.6(5) |
| C(31) | 3590.6(17) | 4007.0(12) | 7908.9(11) | 47.5(4) |
| C(32) | 8184.5(17) | 2764.9(11) | 5863.7(12) | 48.3(4) |
| C(33) | 9202.9(18) | 3328.6(12) | 5709.2(14) | 58.0(5) |
| C(34) | 9634.5(19) | 3971.9(14) | 6395.0(16) | 66.1(5) |
| C(35) | 9049(2) | 4060.9(14) | 7219.6(16) | 67.4(6) |
| C(36) | 8024.5(18) | 3506.4(13) | 7381.7(13) | 58.6(5) |
| C(37) | 7597.6(16) | 2853.0(11) | 6701.5(12) | 46.2(4) |
| C(38) | 6530.9(16) | 2203.6(11) | 6662.8(11) | 45.0(4) |
| C(39) | 5684.3(18) | 2005.7(12) | 7322.4(12) | 52.1(4) |
| C(40) | 4745.0(19) | 1354.1(12) | 7102.1(13) | 57.2(5) |
| C(41) | 4635.2(19) | 912.3(12) | 6237.6(13) | 57.4(5) |
| C(42) | 5474.5(18) | 1102.9(11) | 5573.6(12) | 53.5(5) |
| C(43) | 6431.5(17) | 1747.5(10) | 5788.8(11) | 45.3(4) |
| C(44) | 7514.5(17) | 2037.2(11) | 5216.1(11) | 47.1(4) |
| C(45) | 7092.7(18) | 2505.9(12) | 4345.3(12) | 52.8(4) |
| C(54) | 8376.5(19) | 1211.3(12) | 4976.5(12) | 55.0(5) |
| C(46) | 6343(16) | 1953(13) | 3602(11) | 52(2) |
| C(47) | 5007(13) | 2054(10) | 3505(10) | 64(3) |
| C(48) | 4337(12) | 1596(7) | 2776(9) | 70(2) |
| C(49) | 4914(14) | 1046(11) | 2141(9) | 68(2) |
| C(50) | 6222(10) | 920(10) | 2267(10) | 62(2) |
| C(51) | 6882(14) | 1373(14) | 2994(11) | 58(2) |
| C(52) | 4192(12) | 589(10) | 1356(9) | 90(3) |
| C(53) | 3113(6) | 951(4) | 992(3) | 124(2) |
| C(55) | 8920(20) | 793(14) | 5797(12) | 50(3) |
| C(56) | 8292(12) | 206(8) | 6325(7) | 57(2) |
| C(57) | 8897(11) | −82(6) | 7114(6) | 66(2) |
| C(58) | 10114(10) | 200(7) | 7381(6) | 65(2) |
| C(59) | 10736(10) | 782(8) | 6829(6) | 69(2) |
| C(60) | 10150(13) | 1064(9) | 6053(7) | 64(2) |
| C(61) | 10706(8) | −61(5) | 8237(5) | 93(2) |
| C(62) | 10319(7) | −724(5) | 8731(4) | 137(3) |
| C(46A) | 6280(30) | 1980(20) | 3618(17) | 48(4) |
| C(47A) | 6780(20) | 1330(20) | 2923(17) | 53(4) |
| C(48A) | 5938(17) | 926(16) | 2247(14) | 58(3) |
| C(49A) | 4720(20) | 1136(18) | 2169(13) | 62(3) |
| C(50A) | 4280(20) | 1808(12) | 2829(13) | 59(3) |
| C(51A) | 5080(20) | 2189(16) | 3518(14) | 53(3) |
| C(52A) | 3900(20) | 747(17) | 1394(13) | 86(4) |
| C(53A) | 4311(12) | 105(8) | 726(6) | 150(5) |
| C(55A) | 9040(30) | 830(20) | 5800(20) | 47(3) |
| C(56A) | 10145(19) | 1125(13) | 6270(10) | 54(3) |
| C(57A) | 10560(16) | 703(13) | 7050(9) | 57(3) |
| C(58A) | 9878(18) | 21(12) | 7422(11) | 58(3) |
| C(59A) | 8775(17) | −276(10) | 6945(10) | 57(2) |
| C(60A) | 8400(20) | 114(14) | 6166(12) | 53(3) |
| C(61A) | 10318(11) | −366(7) | 8268(8) | 65(2) |
| C(62A) | 11108(10) | 8(7) | 8895(7) | 111(3) |

TABLE 8

Bond length [Å] and bond angle [°] of p,p-BVBF

| | | | | | |
|---|---|---|---|---|---|
| C(1)-C(2) | 1.279 (4) | C(61)-C(62) | 1.322 (9) | C(35)-C(34)-C(33) | 120.7 (2) |
| C(2)-C(3) | 1.475 (3) | C(46A)-C(47A) | 1.46 (3) | C(34)-C(35)-C(36) | 120.89 (19) |
| C(3)-C(4) | 1.384 (3) | C(46A)-C(51A) | 1.32 (3) | C(35)-C(36)-C(37) | 118.70 (19) |
| C(3)-C(8) | 1.389 (3) | C(47A)-C(48A) | 1.40 (2) | C(32)-C(37)-C(38) | 108.43 (15) |
| C(4)-C(5) | 1.381 (3) | C(48A)-C(49A) | 1.34 (2) | C(36)-C(37)-C(32) | 120.53 (17) |
| C(5)-C(6) | 1.384 (3) | C(49A)-C(50A) | 1.43 (2) | C(36)-C(37)-C(38) | 130.98 (17) |
| C(6)-C(7) | 1.388 (3) | C(49A)-C(52A) | 1.479 (12) | C(39)-C(38)-C(37) | 130.71 (16) |
| C(6)-C(9) | 1.512 (2) | C(50A)-C(51A) | 1.37 (2) | C(39)-C(38)-C(43) | 120.52 (17) |
| C(7)-C(8) | 1.382 (3) | C(52A)-C(53A) | 1.394 (17) | C(43)-C(38)-C(37) | 108.76 (15) |
| C(9)-C(19) | 1.546 (2) | C(55A)-C(56A) | 1.39 (3) | C(40)-C(39)-C(38) | 118.89 (17) |
| C(10)-C(11) | 1.241 (3) | C(55A)-C(60A) | 1.40 (3) | C(39)-C(40)-C(41) | 120.69 (17) |
| C(11)-C(12) | 1.498 (3) | C(56A)-C(57A) | 1.405 (17) | C(40)-C(41)-C(42) | 120.97 (18) |
| C(12)-C(13) | 1.389 (3) | C(57A)-C(58A) | 1.379 (16) | C(43)-C(42)-C(41) | 118.95 (17) |
| C(12)-C(17) | 1.368 (3) | C(58A)-C(59A) | 1.389 (16) | C(38)-C(43)-C(44) | 110.42 (15) |
| C(13)-C(14) | 1.403 (3) | C(58A)-C(61A) | 1.470 (11) | C(42)-C(43)-C(38) | 119.96 (16) |
| C(14)-C(15) | 1.384 (2) | C(59A)-C(60A) | 1.368 (18) | C(42)-C(43)-C(44) | 129.54 (15) |
| C(15)-C(16) | 1.387 (3) | C(61A)-C(62A) | 1.306 (11) | C(32)-C(44)-C(43) | 101.38 (13) |
| C(15)-C(18) | 1.507 (2) | C(1)-C(2)-C(3) | 128.5 (3) | C(32)-C(44)-C(45) | 107.38 (13) |
| C(16)-C(17) | 1.371 (3) | C(4)-C(3)-C(2) | 120.3 (2) | C(32)-C(44)-C(54) | 111.72 (15) |
| C(18)-C(19) | 1.564 (2) | C(4)-C(3)-C(8) | 117.21 (18) | C(43)-C(44)-C(45) | 113.98 (15) |
| C(19)-C(20) | 1.521 (2) | C(8)-C(3)-C(2) | 122.5 (2) | C(43)-C(44)-C(54) | 110.79 (13) |
| C(19)-C(31) | 1.522 (2) | C(5)-C(4)-C(3) | 121.5 (2) | C(45)-C(44)-C(54) | 111.17 (14) |
| C(20)-C(21) | 1.381 (3) | C(4)-C(5)-C(6) | 121.4 (2) | C(46)-C(45)-C(44) | 118.9 (8) |
| C(20)-C(25) | 1.395 (2) | C(5)-C(6)-C(7) | 117.22 (17) | C(46A)-C(45)-C(44) | 119.6 (14) |
| C(21)-C(22) | 1.391 (3) | C(5)-C(6)-C(9) | 121.83 (17) | C(55)-C(54)-C(44) | 113.6 (11) |
| C(22)-C(23) | 1.380 (3) | C(7)-C(6)-C(9) | 120.88 (17) | C(55A)-C(54)-C(44) | 114.4 (18) |
| C(23)-C(24) | 1.374 (3) | C(8)-C(7)-C(6) | 121.41 (19) | C(47)-C(46)-C(45) | 120.3 (13) |
| C(24)-C(25) | 1.387 (3) | C(7)-C(8)-C(3) | 121.2 (2) | C(51)-C(46)-C(45) | 122.2 (13) |
| C(25)-C(26) | 1.461 (3) | C(6)-C(9)-C(19) | 116.73 (14) | C(51)-C(46)-C(47) | 117.5 (7) |
| C(26)-C(27) | 1.396 (3) | C(10)-C(11)-C(12) | 129.2 (3) | C(48)-C(47)-C(46) | 119.9 (10) |
| C(26)-C(31) | 1.397 (2) | C(13)-C(12)-C(11) | 123.3 (2) | C(49)-C(48)-C(47) | 121.6 (11) |
| C(27)-C(28) | 1.377 (3) | C(17)-C(12)-C(11) | 118.9 (2) | C(48)-C(49)-C(50) | 117.9 (7) |
| C(28)-C(29) | 1.380 (3) | C(17)-C(12)-C(13) | 117.7 (2) | C(48)-C(49)-C(52) | 120.7 (10) |
| C(29)-C(30) | 1.387 (3) | C(12)-C(13)-C(14) | 121.01 (19) | C(50)-C(49)-C(52) | 121.4 (10) |
| C(30)-C(31) | 1.383 (3) | C(15)-C(14)-C(13) | 120.58 (19) | C(51)-C(50)-C(49) | 120.4 (11) |
| C(32)-C(33) | 1.384 (3) | C(14)-C(15)-C(16) | 117.07 (18) | C(46)-C(51)-C(50) | 122.7 (11) |
| C(32)-C(37) | 1.401 (2) | C(14)-C(15)-C(18) | 122.19 (17) | C(53)-C(52)-C(49) | 122.5 (9) |
| C(32)-C(44) | 1.521 (2) | C(16)-C(15)-C(18) | 120.68 (16) | C(56)-C(55)-C(54) | 125.5 (14) |
| C(33)-C(34) | 1.385 (3) | C(17)-C(16)-C(15) | 122.24 (18) | C(56)-C(55)-C(60) | 118.8 (7) |
| C(34)-C(35) | 1.383 (3) | C(12)-C(17)-C(16) | 121.4 (2) | C(60)-C(55)-C(54) | 115.6 (13) |
| C(35)-C(36) | 1.384 (3) | C(15)-C(18)-C(19) | 118.05 (15) | C(55)-C(56)-C(57) | 119.2 (11) |
| C(36)-C(37) | 1.387 (2) | C(9)-C(19)-C(18) | 109.36 (13) | C(58)-C(57)-C(56) | 122.1 (9) |
| C(37)-C(38) | 1.462 (2) | C(20)-C(19)-C(9) | 112.96 (14) | C(57)-C(58)-C(59) | 117.6 (6) |
| C(38)-C(39) | 1.391 (2) | C(20)-C(19)-C(18) | 107.23 (14) | C(57)-C(58)-C(61) | 121.5 (8) |
| C(38)-C(43) | 1.402 (2) | C(20)-C(19)-C(31) | 101.39 (14) | C(59)-C(58)-C(61) | 120.9 (8) |
| C(39)-C(40) | 1.379 (3) | C(31)-C(19)-C(9) | 113.05 (15) | C(60)-C(59)-C(58) | 120.6 (9) |
| C(40)-C(41) | 1.382 (3) | C(31)-C(19)-C(18) | 112.56 (14) | C(59)-C(60)-C(55) | 121.6 (11) |
| C(41)-C(42) | 1.388 (3) | C(21)-C(20)-C(19) | 129.15 (16) | C(62)-C(61)-C(58) | 126.4 (8) |
| C(42)-C(43) | 1.385 (2) | C(21)-C(20)-C(25) | 120.00 (17) | C(47A)-C(46A)-C(45) | 123 (2) |
| C(43)-C(44) | 1.525 (2) | C(25)-C(20)-C(19) | 110.78 (16) | C(51A)-C(46A)-C(45) | 119.0 (19) |
| C(44)-C(45) | 1.553 (2) | C(20)-C(21)-C(22) | 118.88 (19) | C(51A)-C(46A)-C(47A) | 117.2 (11) |
| C(44)-C(54) | 1.561 (2) | C(23)-C(22)-C(21) | 120.6 (2) | C(48A)-C(47A)-C(46A) | 118.1 (16) |
| C(45)-C(46) | 1.504 (7) | C(24)-C(23)-C(22) | 121.0 (2) | C(49A)-C(48A)-C(47A) | 123.6 (15) |
| C(45)-C(46A) | 1.507 (11) | C(23)-C(24)-C(25) | 118.72 (19) | C(48A)-C(49A)-C(50A) | 116.6 (11) |
| C(54)-C(55) | 1.497 (7) | C(20)-C(25)-C(26) | 108.53 (15) | C(48A)-C(49A)-C(52A) | 121.4 (15) |
| C(54)-C(55A) | 1.522 (11) | C(24)-C(25)-C(20) | 120.78 (18) | C(50A)-C(49A)-C(52A) | 121.8 (16) |
| C(46)-C(47) | 1.437 (17) | C(24)-C(25)-C(26) | 130.68 (17) | C(51A)-C(50A)-C(49A) | 120.5 (17) |
| C(46)-C(51) | 1.340 (17) | C(27)-C(26)-C(25) | 130.82 (17) | C(46A)-C(51A)-C(50A) | 123.8 (17) |
| C(47)-C(48) | 1.386 (14) | C(27)-C(26)-C(31) | 120.39 (18) | C(53A)-C(52A)-C(49A) | 123.2 (16) |
| C(48)-C(49) | 1.360 (14) | C(31)-C(26)-C(25) | 108.79 (15) | C(56A)-C(55A)-C(54) | 130 (2) |
| C(49)-C(50) | 1.416 (13) | C(28)-C(27)-C(26) | 118.94 (19) | C(56A)-C(55A)-C(60A) | 114.8 (11) |
| C(49)-C(52) | 1.470 (7) | C(27)-C(28)-C(29) | 120.8 (2) | C(60A)-C(55A)-C(54) | 115 (2) |
| C(50)-C(51) | 1.375 (15) | C(28)-C(29)-C(30) | 120.5 (2) | C(55A)-C(56A)-C(57A) | 120.8 (16) |
| C(52)-C(53) | 1.382 (13) | C(31)-C(30)-C(29) | 119.48 (19) | C(58A)-C(57A)-C(56A) | 123.0 (14) |
| C(55)-C(56) | 1.38 (2) | C(26)-C(31)-C(19) | 110.47 (16) | C(57A)-C(58A)-C(59A) | 116.1 (10) |
| C(55)-C(60) | 1.39 (2) | C(30)-C(31)-C(19) | 129.73 (17) | C(57A)-C(58A)-C(61A) | 121.1 (12) |
| C(56)-C(57) | 1.402 (12) | C(30)-C(31)-C(26) | 119.79 (17) | C(59A)-C(58A)-C(61A) | 122.9 (12) |
| C(57)-C(58) | 1.385 (11) | C(33)-C(32)-C(37) | 120.12 (17) | C(60A)-C(59A)-C(58A) | 120.6 (14) |
| C(58)-C(59) | 1.393 (10) | C(33)-C(32)-C(44) | 128.98 (17) | C(59A)-C(60A)-C(55A) | 124.5 (17) |
| C(58)-C(61) | 1.467 (7) | C(37)-C(32)-C(44) | 110.85 (15) | C(62A)-C(61A)-C(58A) | 127.5 (10) |
| C(59)-C(60) | 1.376 (12) | C(32)-C(33)-C(34) | 119.09 (19) | | |

TABLE 9

| Anisotropic displacement parameters (Å$^2$ × 10$^3$) of p,p-BVBF | | | | | | |
|---|---|---|---|---|---|---|
| C(1) | 174(3) | 98(2) | 72.0(16) | −9.4(15) | 22.0(19) | 56(2) |
| C(2) | 109(2) | 95.9(18) | 69.6(15) | −1.7(14) | 25.9(14) | 38.0(16) |
| C(3) | 71.9(14) | 65.6(12) | 55.7(11) | 7.4(10) | 12.6(10) | 24.1(11) |
| C(4) | 48.9(11) | 85.8(15) | 69.7(13) | 5.6(11) | 15.1(10) | 12.8(10) |
| C(5) | 45.5(11) | 70.8(12) | 64.8(12) | −4.0(10) | 1.1(9) | 6.0(9) |
| C(6) | 52.0(10) | 51.8(10) | 44.5(9) | 7.2(8) | 1.5(8) | 14.5(8) |
| C(7) | 68.9(13) | 48.0(10) | 55.2(11) | 10.9(8) | 14.1(9) | 6.9(9) |
| C(8) | 87.6(15) | 48.1(10) | 57.6(11) | 3.1(9) | 9.5(11) | 9.9(10) |
| C(9) | 59.8(11) | 56.3(10) | 42.1(9) | 6.8(8) | 2.2(8) | 14.9(9) |
| C(10) | 97(2) | 162(3) | 64.4(15) | 0.8(17) | −2.1(15) | 7(2) |
| C(11) | 72.7(15) | 111.5(19) | 62.3(13) | −5.6(13) | 10.5(11) | 3.9(13) |
| C(12) | 55.5(11) | 93.7(12) | 53.5(11) | −7.0(10) | 19.1(8) | 10.3(10) |
| C(13) | 75.6(14) | 90.1(11) | 42.2(10) | 14.6(10) | 8.9(10) | 32.1(11) |
| C(14) | 80.4(14) | 60.1(11) | 43.6(10) | 9.6(8) | 11.2(10) | 16.6(10) |
| C(15) | 52.2(10) | 54.5(10) | 39.6(9) | 5.0(7) | 13.7(8) | 13.3(8) |
| C(16) | 68.2(13) | 55.6(11) | 47.3(10) | 7.0(8) | 13.6(9) | 10.0(9) |
| C(17) | 65.1(13) | 66.4(12) | 59.2(12) | 0.3(10) | 17.7(10) | 1.4(10) |
| C(18) | 54.4(11) | 59.8(11) | 46.0(9) | 4.3(8) | 11.2(8) | 9.6(9) |
| C(19) | 50.1(10) | 52.1(10) | 41.5(9) | 5.3(7) | 6.0(7) | 9.7(8) |
| C(20) | 48.7(10) | 51.9(10) | 45.8(9) | −0.3(8) | 8.4(8) | 9.5(8) |
| C(21) | 62.3(12) | 62.8(12) | 58.3(11) | 4.5(9) | 11.1(10) | 3.0(10) |
| C(22) | 61.0(13) | 72.9(13) | 70.5(13) | −8.9(11) | 9.8(11) | −6.6(10) |
| C(23) | 61.4(13) | 86.8(15) | 57.6(12) | −8.9(11) | 0.5(10) | 7.5(12) |
| C(24) | 60.9(12) | 72.5(13) | 46.9(10) | −0.3(9) | 2.1(9) | 14.3(10) |
| C(25) | 51.7(10) | 57.1(10) | 40.5(9) | −0.1(8) | 7.3(8) | 13.8(8) |
| C(26) | 57.9(11) | 51.1(10) | 39.1(9) | 1.5(7) | 9.4(8) | 13.1(8) |
| C(27) | 83.4(15) | 63.8(12) | 44.2(10) | 10.0(9) | 11.3(10) | 11.0(11) |
| C(28) | 98.2(18) | 61.2(12) | 58.2(12) | 9.8(10) | 24.4(12) | −2.4(12) |
| C(29) | 74.9(14) | 62.6(12) | 64.4(13) | −3.5(10) | 24.2(11) | −6.9(10) |
| C(30) | 55.2(11) | 63.1(11) | 51.5(10) | −1.8(9) | 10.9(9) | 6.2(9) |
| C(31) | 49.8(10) | 50.2(9) | 43.2(9) | 1.5(7) | 11.8(8) | 11.3(8) |
| C(32) | 50.9(10) | 38.7(8) | 56.1(10) | 4.5(7) | 8.1(8) | 7.5(7) |
| C(33) | 52.0(11) | 51.8(10) | 71.1(12) | 5.6(9) | 10.6(9) | 4.3(9) |
| C(34) | 47.8(11) | 57.4(11) | 92.6(16) | 7.0(11) | −5.7(11) | −1.7(9) |
| C(35) | 56.2(13) | 62.9(12) | 79.8(15) | −8.6(11) | −14.9(11) | 2.7(10) |
| C(36) | 56.4(12) | 60.9(11) | 56.7(11) | −5.9(9) | −5.1(9) | 10.1(9) |
| C(37) | 48.2(10) | 41.1(8) | 49.2(9) | 0.5(7) | 0.7(8) | 9.3(7) |
| C(38) | 51.4(10) | 39.5(8) | 45.1(9) | 3.2(7) | 7.7(8) | 11.2(7) |
| C(39) | 62.0(12) | 52.6(10) | 42.7(9) | 4.2(8) | 8.3(8) | 12.6(9) |
| C(40) | 68.1(13) | 50.5(10) | 56.1(11) | 13.3(9) | 21.1(9) | 6.2(9) |
| C(41) | 67.6(13) | 42.5(9) | 63.3(12) | 6.5(8) | 15.6(10) | −5.0(9) |
| C(42) | 72.5(13) | 37.3(9) | 50.5(10) | −0.8(7) | 12.4(9) | −3.5(8) |
| C(43) | 56.2(10) | 35.1(8) | 45.4(9) | 3.6(7) | 9.1(8) | 5.7(7) |
| C(44) | 57.5(11) | 39.1(8) | 45.5(9) | 2.6(7) | 13.0(8) | 3.5(7) |
| C(45) | 65.3(12) | 43.0(9) | 51.5(10) | 7.2(8) | 14.3(9) | 1.6(8) |
| C(54) | 68.7(12) | 45.6(9) | 52.2(10) | 2.4(8) | 19.6(9) | 9.6(9) |
| C(46) | 61(4) | 48(4) | 51(5) | 18(4) | 12(4) | 1(3) |
| C(47) | 62(4) | 67(5) | 65(4) | 8(3) | 25(3) | −4(3) |
| C(48) | 63(3) | 74(5) | 73(4) | 8(3) | 6(3) | −11(3) |
| C(49) | 79(5) | 63(4) | 64(4) | 13(3) | 3(4) | −12(3) |
| C(50) | 76(4) | 54(3) | 57(3) | 11(3) | 11(3) | 5(3) |
| C(51) | 72(4) | 54(5) | 50(4) | 13(3) | 7(3) | 2(3) |
| C(52) | 105(6) | 88(5) | 76(5) | 4(4) | −6(4) | −17(4) |
| C(53) | 143(5) | 154(5) | 73(3) | 28(3) | −30(3) | −36(4) |
| C(55) | 53(5) | 39(4) | 58(4) | −6(3) | 12(3) | 8(3) |
| C(56) | 67(3) | 50(3) | 56(3) | 9(3) | 13(3) | 9(3) |
| C(57) | 85(4) | 56(4) | 59(4) | 8(3) | 9(3) | 13(3) |
| C(58) | 70(5) | 64(5) | 61(3) | −3(3) | 7(3) | 32(3) |
| C(59) | 59(3) | 69(3) | 80(5) | −2(3) | 7(3) | 20(3) |
| C(60) | 64(3) | 59(3) | 70(4) | −1(3) | 15(3) | 14(2) |
| C(61) | 98(5) | 97(5) | 85(4) | −2(4) | −10(4) | 44(4) |
| C(62) | 167(6) | 167(6) | 86(4) | 40(4) | 0(4) | 79(5) |
| C(46A) | 71(8) | 40(6) | 36(6) | 2(5) | 20(6) | −2(6) |
| C(47A) | 76(7) | 44(6) | 39(6) | −2(5) | 20(5) | 4(5) |
| C(48A) | 82(7) | 50(5) | 41(5) | −7(4) | 20(5) | −12(5) |
| C(49A) | 78(6) | 64(6) | 45(5) | 5(4) | 19(4) | −18(5) |
| C(50A) | 71(5) | 57(5) | 50(5) | 3(4) | 16(4) | −12(4) |
| C(51A) | 73(6) | 48(4) | 39(5) | 4(3) | 14(5) | −9(4) |
| C(52A) | 105(9) | 93(8) | 59(6) | 0(5) | 9(6) | −13(7) |
| C(53A) | 185(10) | 173(10) | 85(6) | −36(6) | −8(6) | −22(8) |
| C(55A) | 53(7) | 37(6) | 53(6) | 3(5) | 19(5) | 8(5) |
| C(56A) | 52(5) | 43(4) | 67(6) | 1(4) | 14(5) | 1(3) |
| C(57A) | 52(5) | 59(5) | 60(5) | 0(4) | 2(4) | 8(4) |
| C(58A) | 62(5) | 48(4) | 65(4) | 2(3) | 11(4) | 9(3) |
| C(59A) | 67(5) | 44(5) | 59(5) | 0(4) | 9(4) | 2(3) |

TABLE 9-continued

| Anisotropic displacement parameters ($Å^2 \times 10^3$) of p,p-BVBF | | | | | | |
|---|---|---|---|---|---|---|
| C(60A) | 57(5) | 44(4) | 56(5) | −3(4) | 10(4) | 6(4) |
| C(61A) | 72(5) | 59(5) | 68(4) | 19(4) | 7(4) | 7(3) |
| C(62A) | 147(8) | 102(6) | 85(6) | 14(5) | −16(6) | 31(6) |

Example 4

350 mL of acetonitrile, 1.4 mol of potassium t-butoxide, 30 g of PEG-400, and 0.5 g of polymerization inhibitor 701 were added to a reaction flask, and 0.6 mol of fluorene and 1.4 mol of 4-vinylbenzyl chloride (HPLC 99.5%) were then added thereto while stirring. At a temperature of 30-35° C. and a stirring speed of 350 r/min, the resulting mixture was subjected to reaction until the content of fluorene was lower than 1 wt % according to HPLC analysis. The reaction was stopped, and acetonitrile was distilled off. 500 mL of water and 500 mL of toluene were added thereto for layering. The obtained organic phase was washed with a saturated ammonium chloride solution, and washed with water for 3 times (500 mL of water for each time) until neutral. Toluene was distilled off under reduced pressure, and a mixed solvent of toluene and methanol in a volume ratio of 1:0.3 was added thereto. The resulting mixture was heated until being fully dissolved, and cooled at a cooling rate of 0.5° C./min to 5° C. for crystallization at constant temperature. The resulting system was then filtered, and the resulting solid component was dried at 90° C. to constant weight so as to obtain 202.3 g of a 9,9-bis(4-vinylbenzyl)-9H-fluorene which was a white crystal having an HPLC purity of 99.5%, with a yield of 84.5%.

The nuclear magnetic resonance hydrogen spectrum ($^1H$ NMR), nuclear magnetic resonance carbon spectrum ($^{13}C$ NMR) and infrared spectrum (FT-IR) of the synthetic bis (vinylbenzyl) fluorene product of the present disclosure completely conformed with the structure of the single isomer of bis(vinylbenzyl) fluorene, namely 9,9-bis(2-vinylbenzyl)-9H-fluorene (o,o-BVBF) and 9,9-bis(4-vinylbenzyl)-9H-fluorene (p,p.-BVBF) respectively. Here, in the nuclear magnetic resonance hydrogen spectrum of o,o-BVBF, what each peak corresponded to was determined by a two-dimensional diagram of a DQF-COSY $^1H$-$^1H$ correlation nuclear magnetic resonance spectrum. The single-crystal structure of the product obtained through recrystallization from a mixed toluene-methanol solvent (volume ratio=1:1) was determined by using Bruker D8 Venture single-crystal diffractometer, and it was further confirmed that the single isomer 9,9-bis(2-vinylbenzyl)-9H-fluorene and 9,9-bis(4-vinylbenzyl)-9H-fluorene were successfully prepared in the present disclosure.

The 9,9-bis(2-vinylbenzyl)-9H-fluorene, 9,9-bis(4-vinylbenzyl)-9H-fluorene, or a mixture thereof in any ratio was capable of completely dissolving in toluene and 2-butanone at room temperature (25° C.) to form a clear solution. Here, the mass ratio of bis(vinylbenzyl) fluorene to toluene was 1:1, and the mass ratio of bis(vinylbenzyl) fluorene to 2-butanone was 1:1. By contrast, the 1,2-bis(4-vinylphenyl) ethane (BVPE, CAS: 48174-52-3, as a crosslinker commonly used in a printed circuit substrate resin), and the bis(vinylbenzyl) fluorene containing a meta isomer in the comparative example only had a solubility of 20% in toluene or 2-butanone, which indicated that the 9,9-bis(2-vinylbenzyl)-9H-fluorene and 9,9-bis(4-vinylbenzyl)-9H-fluorene prepared in the present disclosure had much higher solubility in an organic solvent compared with 1,2-bis(4-vinylphenyl) ethane and the meta isomer of bis(vinylbenzyl) fluorene.

Example 5

The 9,9-bis(2-vinylbenzyl)-9H-fluorene prepared in Example 1 was made into a 80 mm×80 mm×0.4 mm resin sheet through a melting pouring method (thermal solidification conditions: a temperature being 200° C., a pressure being 70-80 mmHg, a time being 30 min), and the dielectric constant and dielectric dissipation factor of the sample at a frequency of 10 GHz were determined by using a U.S. Agilent N5230A vector network analyzer. The results are shown in Table 10.

Example 6

The 9,9-bis(4-vinylbenzyl)-9H-fluorene prepared in Example 3 was made into a 80 mm×80 mm×0.4 mm resin sheet through a melting pouring method (thermal solidification conditions: a temperature being 200° C., a pressure being 70-80 mmHg, and a time being 30 min), and the dielectric constant and dielectric dissipation factor of the sample at a frequency of 10 GHz were determined by using a U.S. Agilent N5230A vector network analyzer. The results are shown in Table 10.

Example 7

20 wt % of the 9,9-bis(2-vinylbenzyl)-9H-fluorene prepared in Example 1 and 80 wt % of the 9,9-bis(4-vinylbenzyl)-9H-fluorene prepared in Example 3 were made into a 80 mm×80 mm×0.4 mm resin sheet through a melting pouring method (thermal solidification conditions: a temperature being 200° C., a pressure being 70-80 mmHg, and a time being 30 min), and the dielectric constant and dielectric dissipation factor of the sample at a frequency of 10 GHz were determined by using a U.S. Agilent N5230A vector network analyzer. The results are shown in Table 10.

Example 8

40 wt % of the 9,9-bis(2-vinylbenzyl)-9H-fluorene prepared in Example 1 and 60 wt % of the 9,9-bis(4-vinylbenzyl)-9H-fluorene prepared in Example 3 were made into a 80 mm×80 mm×0.4 mm resin sheet through a melting pouring method (thermal solidification conditions: a temperature being 200° C., a pressure being 70-80 mmHg, and a time being 30 min), and the dielectric constant and dielectric dissipation factor of the sample at a frequency of 10 GHz were determined by using a U.S. Agilent N5230A vector network analyzer. The results are shown in Table 10.

Example 9

60 wt % of the 9,9-bis(2-vinylbenzyl)-9H-fluorene prepared in Example 1 and 40 wt % of the 9,9-bis(4-vinylbenzyl)-9H-fluorene prepared in Example 3 were made into a 80 mm×80 mm×0.4 mm resin sheet through a melting pouring method (thermal solidification conditions: a temperature being 200° C., a pressure being 70-80 mmHg, and a time being 30 min), and the dielectric constant and dielectric dissipation factor of the sample at a frequency of 10 GHz were determined by using a U.S. Agilent N5230A vector network analyzer. The results are shown in Table 10.

Example 10

80 wt % of the 9,9-bis(2-vinylbenzyl)-9H-fluorene prepared in Example 1 and 20 wt % of the 9,9-bis(4-vinylbenzyl)-9H-fluorene prepared in Example 3 were made into a 80 mm×80 mm×0.4 mm resin sheet through a melting pouring method (thermal solidification conditions: a temperature being 200° C., a pressure being 70-80 mmHg, and a time being 30 min), and the dielectric constant and dielectric dissipation factor of the sample at a frequency of 10 GHz were determined by using a U.S. Agilent N5230A vector network analyzer. The results are shown in Table 10.

Comparative Example 1

1,2-bis(4-vinylphenyl) ethane (BVPE) was made into a 80 mm×80 mm×0.4 mm resin sheet through a melting pouring method (thermal solidification conditions: a temperature being 200° C., a pressure being 70-80 mmHg, and a time being 30 min), and the dielectric constant and dielectric dissipation factor of the sample at a frequency of 10 GHz were determined by using a U.S. Agilent N5230A vector network analyzer. The results are shown in Table 10.

Comparative Example 2

This comparative example was performed similarly as the method in Example 1 of patent publication CN1501899A (incorporated by reference), and a mixture of 3-vinylbenzyl chloride and 4-vinylbenzyl chloride in a mass ratio of 1:1 was used as a raw material to synthesize a 9,9-bis(vinylbenzyl)-9H-fluorene mixture containing a meta isomer and a para isomer. The 9,9-bis(vinylbenzyl)-9H-fluorene mixture were recrystallized from toluene to obtain a crystal having a melting point of 142-145° C.

The resulting 9,9-bis(vinylbenzyl)-9H-fluorene mixture containing the meta isomer and the para isomer was made into a 80 mm×80 mm×0.4 mm resin sheet through a melting pouring method (thermal solidification conditions: a temperature being 200° C., a pressure being 70-80 mmHg, and a time being 30 min), and the dielectric constant and dielectric dissipation factor of the sample at a frequency of 10 GHz were determined by using a U.S. Agilent N5230A vector network analyzer. The results are shown in Table 10.

a dielectric dissipation factor that are much smaller than those of a 1,2-bis(4-vinylphenyl) ethane resin sample (Comparative Example 1) and a sample containing a meta-isomer of bis(vinylbenzyl)-9H-fluorene (Comparative Example 2). As for the test on the resin sample of a mixture of 9,9-bis(2-vinylbenzyl)-9H-fluorene and 9,9-bis(4-vinylbenzyl)-9H-fluorene in different ratios, a higher content of 9,9-bis(2-vinylbenzyl)-9H-fluorene results in a smaller dielectric dissipation factor of the resin. When the content of 9,9-bis(2-vinylbenzyl)-9H-fluorene is 20 wt % or higher, the dielectric dissipation factor of the resin is 0.00044 or less. The bis(vinylbenzyl) fluorene hydrocarbon resin provided by the present disclosure has a low dielectric constant and a small dielectric dissipation factor, and could be used as a principal resin for a high-frequency substrate or a crosslinking agent for an alkenyl resin component.

The foregoing descriptions are merely preferred embodiments of the present disclosure, and it should be noted that for ordinary artisans in the art, without departing from the principles of the present disclosure, some improvements and refinement may also be made, which should also be considered as falling within the scope of the present disclosure.

What is claimed is:

1. A bis(vinylbenzyl) fluorene, being 9,9-bis(2-vinylbenzyl)-9H-fluorene having a structure shown in formula I or 9,9-bis(4-vinylbenzyl)-9H-fluorene having a structure shown in formula II:

formula I

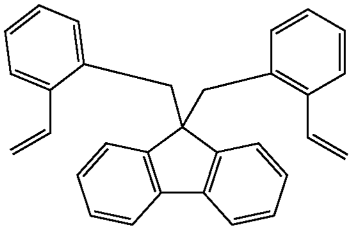
, formula II

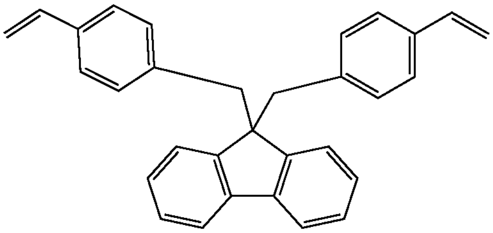
;

TABLE 10

Dielectric constant $D_k$ (10 GHz) and dielectric dissipation factor $D_f$ (10 GHz) of resin sheets prepared in Examples 5-10 and Comparative Examples 1-2

| | Example 5 | Example 6 | Example 7 | Example 8 | Example 9 | Example 10 | Comparative Example 1 | Comparative Example 2 |
|---|---|---|---|---|---|---|---|---|
| $D_k$ (10 GHz) | 2.8 | 2.8 | 2.8 | 2.8 | 2.8 | 2.8 | 3.2 | 2.8 |
| $D_f$ (10 GHz) | 0.00032 | 0.00047 | 0.00044 | 0.00041 | 0.00038 | 0.00035 | 0.00080 | 0.00065 |

As can be seen from Table 10, the dielectric dissipation factor of 9,9-bis(2-vinylbenzyl)-9H-fluorene is smaller than that of 9,9-bis(4-vinylbenzyl)-9H-fluorene, and the two compounds mentioned above have a dielectric constant and wherein the 9,9-bis(2-vinylbenzyl)-9H-fluorene has a monoclinic crystal system;

the 9,9-bis(4-vinylbenzyl)-9H-fluorene has a triclinic crystal system.

2. The bis(vinylbenzyl) fluorene as claimed in claim 1, wherein 2θ characteristic peaks of a powder X-ray diffraction analysis of the 9,9-bis(2-vinylbenzyl)-9H-fluorene comprises 11.9°, 12.3°, 14.2°, 15.4°, 18.5°, 19.2°, 20.0°, 20.7°, 22.2°, 23.7°, and 24.7°.

3. The bis(vinylbenzyl) fluorene as claimed in claim 1, wherein the 9,9-bis(2-vinylbenzyl)-9H-fluorene has a space group of $P2_1/c$, and unit-cell dimensions as follows: a=20.0139(5)Å, α=90°, b=10.9697(3)Å, β=96.243 (2)°, c=10.1983(3)Å, and γ=90°.

4. The bis(vinylbenzyl) fluorene as claimed in claim 1, wherein the 9,9-bis(2-vinylbenzyl)-9H-fluorene has a melting point of 124-126° C.

5. The bis(vinylbenzyl) fluorene as claimed in claim 1, wherein 2θ characteristic peaks of a powder X-ray diffraction analysis of the 9,9-bis(4-vinylbenzyl)-9H-fluorene comprises 11.1°, 12.0°, 18.6°, 19.1°, 20.0°, 22.1°, 23.6°, 24.0° and 24.6°.

6. The bis(vinylbenzyl) fluorene as claimed in claim 1, wherein the 9,9-bis(4-vinylbenzyl)-9H-fluorene has a space group of $P\bar{1}$, and unit-cell dimensions as follows: a=10.6519 (6)Å, α=94.299(2) °, b=14.6326(7)Å, β=92.157(2)°, c=14.7009(8)Å, and γ=91.265(3)°.

7. The bis(vinylbenzyl) fluorene as claimed in claim 1, wherein the 9,9-bis(4-vinylbenzyl)-9H-fluorene has a melting point of 118-120° C.

8. A method for preparing the bis(vinylbenzyl) fluorene as claimed in claim 1, comprising:

mixing fluorene, vinylbenzyl chloride, a basic reagent, a polymerization inhibitor, a phase-transfer catalyst, and an organic solvent, and subjecting a resulting mixture to phase transfer reaction, to obtain the bis(vinylbenzyl) fluorene, wherein the vinylbenzyl chloride is 2-vinylbenzyl chloride or 4-vinylbenzyl chloride.

9. The method as claimed in claim 8, wherein the phase-transfer catalyst comprises at least one selected from the group consisting of a quaternary ammonium salt, a quaternary phosphonium salt, and polyethylene glycol; a mass of the phase-transfer catalyst is 10-35% of a mass of the fluorene; and the organic solvent comprises at least one selected from the group consisting of an aromatic hydrocarbon, an aliphatic hydrocarbon, petroleum ether, and acetonitrile.

10. The method as claimed in claim 9, wherein the polyethylene glycol has a number-average molecular weight of 200-600.

11. The method as claimed in claim 8, wherein the basic reagent comprises at least one selected from the group consisting of an alkali metal hydroxide and an alkali metal alkoxide; and a molar ratio of the fluorene to the basic reagent is in a range of 1:1.8 to 1:5.

12. The method as claimed in claim 8, wherein the phase transfer reaction is performed at a temperature of 25-45° C. for 12-18 h, and the phase transfer reaction is performed with stirring.

13. The method as claimed in claim 8, wherein the polymerization inhibitor comprises at least one selected from the group consisting of nitromethane, nitrobenzene, o-nitrophenol, phenothiazine, 2-phenylnaphthylamine, hydroquinone, catechol, p-methoxyphenol, 2,6-di-tert-butyl-p-cresol, p-tert-butyl-catechol, 2,2,6,6-tetramethylpiperidine oxynitride, and 2,2,6,6-tetramethyl-4-hydroxypiperidine oxynitride; and a mass of the polymerization inhibitor is 0.01-0.5% of a mass of the vinylbenzyl chloride.

14. The method as claimed in claim 8, wherein a molar ratio of the fluorene to the vinylbenzyl chloride is in a range of 1:2 to 1:2.5.

* * * * *